United States Patent [19]

Tsushima et al.

[11] Patent Number: 4,480,118

[45] Date of Patent: Oct. 30, 1984

[54] CARBOXYLIC ACID ESTER AND AN INSECTICIDAL AND/OR ACARICIDAL COMPOSITION CONTAINING THE SAME

[75] Inventors: Kazunori Tsushima, Nishinomiya; Noritada Matsuo, Itami; Makoto Hatakoshi, Minoo; Toshihiko Yano, Ikoma; Nobushige Itaya, Nishinomiya, all of Japan

[73] Assignee: Sumitomo Chemical Company, Limited, Osaka, Japan

[21] Appl. No.: 335,618

[22] Filed: Dec. 30, 1981

[30] Foreign Application Priority Data

Jan. 13, 1981 [JP] Japan .................. 56-4066
Apr. 7, 1981 [JP] Japan .................. 56-52628
May 20, 1981 [JP] Japan .................. 56-77018

[51] Int. Cl.³ .......................................... C07L 69/76
[52] U.S. Cl. ................................. 560/8; 260/465 D; 260/544 D; 562/405; 546/285; 548/308; 548/513; 549/71; 549/330; 549/462; 549/505; 424/308; 424/256; 424/272; 424/283; 424/284
[58] Field of Search .......... 560/8; 260/465 D, 544 D; 546/285; 548/308, 573; 549/71, 330, 462, 505; 424/308, 256, 272, 283, 284; 562/405

[56] References Cited

U.S. PATENT DOCUMENTS 4,072,752  2/1978  Faroog et al. ............. 560/8
4,083,863  4/1978  Brand ........................ 560/8
4,203,918  5/1980  Brown ....................... 560/8
4,317,834  3/1982  Fuchs ........................ 560/8
4,358,607 11/1982  Brown ....................... 560/8

FOREIGN PATENT DOCUMENTS 2642814  7/1977  Fed. Rep. of Germany ........ 560/8

*Primary Examiner*—Paul J. Killos
*Attorney, Agent, or Firm*—Stevens, Davis, Miller & Mosher

[57] ABSTRACT

This invention relates to a novel carboxylic acid ester represented by the following general formula (I) and an insecticidal and/or acaricidal composition containing the same as an active ingredient:

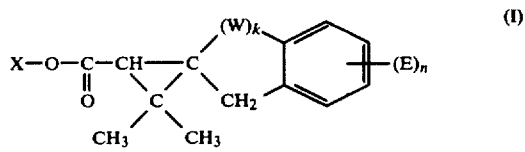

wherein X is represented by the formula,

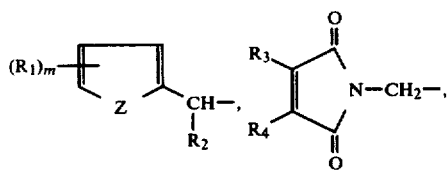

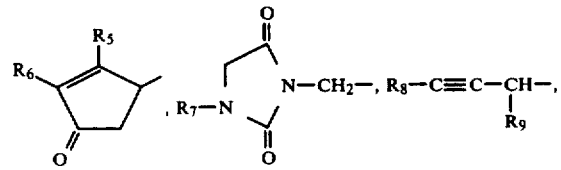

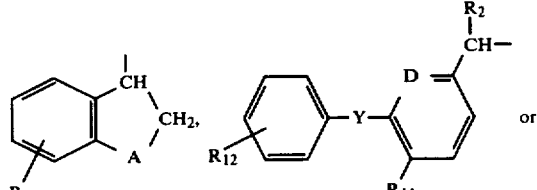

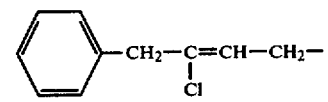

and further also relates to a carboxylic acid or a reactive derivative thereof represented by the general formula,

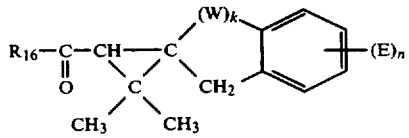

wherein $R_{16}$ is hydroxy group, chlorine or bromine atom, or a $C_{1-2}$ alkoxy group, W is oxygen atom or $-CH_2-$ group, k is an integer of 0 or 1, E is hydrogen, chlorine, fluorine or bromine atom, and n is an integer of 1 to 4.

35 Claims, No Drawings

CARBOXYLIC ACID ESTER AND AN INSECTICIDAL AND/OR ACARICIDAL COMPOSITION CONTAINING THE SAME

This invention relates to a novel carboxylic acid ester represented by the following general formula (I) and an insecticidal and/or acaricidal composition containing said carboxylic acid ester as the active ingredient:

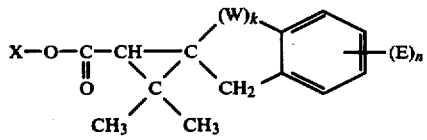
(I)

wherein X is represented by the formula,

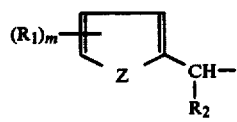
(II)

$R_1$ being hydrogen or halogen atom, or methyl, 2-propenyl, 2-propynyl, benzyl, 2-cyclopenten-1-yl, thienyloxy or thenyl group, $R_2$ being hydrogen atom, or ethynyl, cyano or 1-propynyl group, Z being oxygen or sulfur atom, or —CH=CH— group and m being an integer of 1 to 3 when Z is oxygen or sulfur atom and being an integer of 1 to 5 when Z is —CH=CH— group, provided that when $R_1$ is benzyl group, Z is oxygen or sulfur atom;

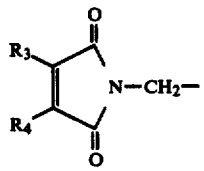
(III)

$R_3$ and $R_4$ being methyl group or bonded at the ends to form tetramethylene chain;

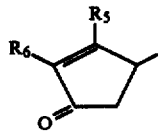
(IV)

$R_5$ being hydrogen atom or methyl group and $R_6$ being benzyl, 1-buten-3-yl or 1-butyn-3-yl group when $R_5$ is hydrogen atom and $R_6$ being ethyl, 2-propenyl, 3-chloro-2-propenyl or 2-propynyl group when $R_5$ is methyl group;

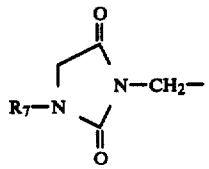
(V)

$R_7$ being 2-propenyl or 2-propynyl group;

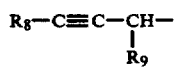
(VI)

$R_8$ being hydrogen atom or methyl group and $R_9$ being a group of the formula,

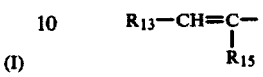

($R_{13}$ is $C_{1-3}$ alkyl, 2-propenyl, 2-propynyl or benzyl group and $R_{15}$ is hydrogen atom or methyl group) or $R_{14}$—C≡C— ($R_{14}$ is hydrogen atom or $C_{1-3}$ alkyl, 2-propenyl, 2-propynyl or benzyl group);

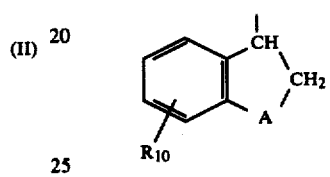
(VII)

$R_{10}$ being hydrogen or halogen atom, or methyl or 2-propenyl group and A being oxygen atom or methylene group;

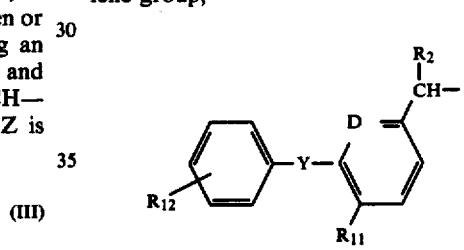
(VIII)

$R_{11}$ being hydrogen or fluorine atom, $R_{12}$ being hydrogen, chlorine, fluorine or bromine atom, D being CH group or nitrogen atom, and Y being oxygen or sulfur atom, or —CH$_2$— or —NH— group, and $R_2$ being as defined above; or

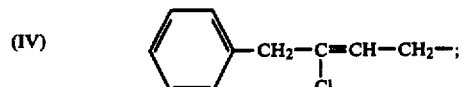
(IX)

W is oxygen atom or —CH$_2$— group; k is an integer of 0 or 1; E is hydrogen, chlorine, fluorine or bromine atom; and n is an integer of 1 to 4, and further, this invention relates also to a carboxylic acid or a reactive derivative thereof represented by the general formula (X),

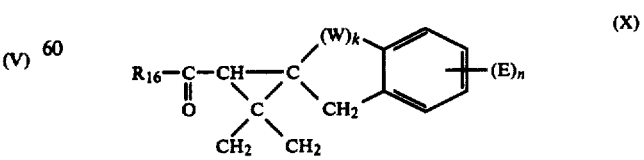
(X)

wherein $R_{16}$ is hydroxy group, chlorine or bromine atom, or a $C_{1-2}$ alkoxy group, W is oxygen atom or —CH$_2$— group, k is an integer of 0 or 1, E is hydrogen, chlorine, fluorine or bromine atom, and n is an integer of 1 to 4.

The present inventors conducted extensive studies for the purpose of developing a compound having an excellent insecticidal and/or acaricidal activity. As a result, it was found that the compounds represented by the general formula (I) have such characteristics as (1) a high insecticidal and/or acaricidal activity which is rapid effect, (2) little residual toxicity to the environment, (3) a comparatively low toxicity to mammals, and (4) a high activity even against those insect pests which are resistant to organophosphorous or carbamate pesticides. These characteristics were found to be preferably pronounced when X of the general formula is represented by the formula (VIII) wherein Y is oxygen atom and D is CH, and E is chlorine, fluorine or hydrogen atom, and more preferably pronounced in the following formulas.

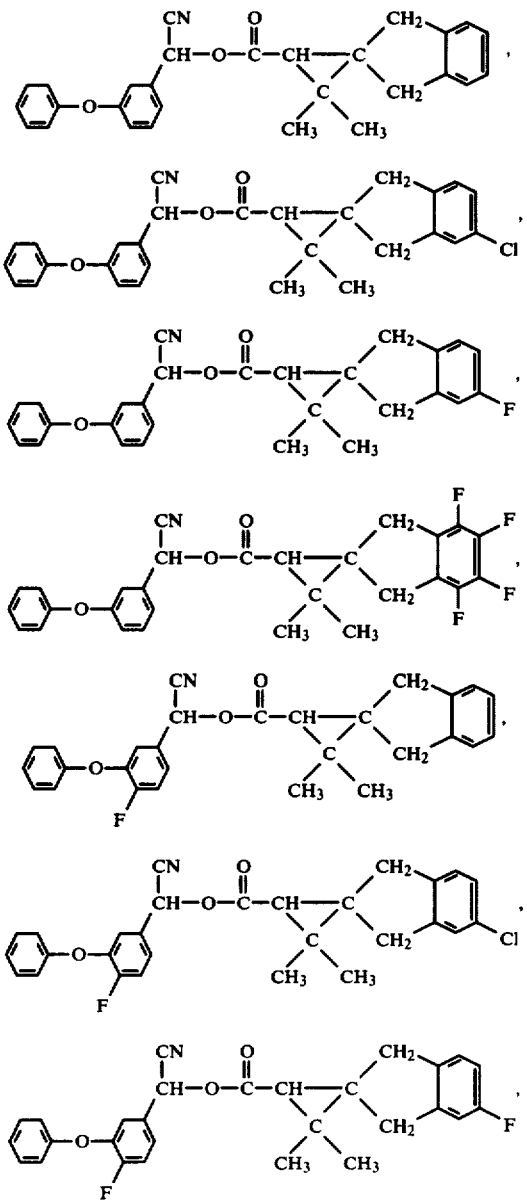

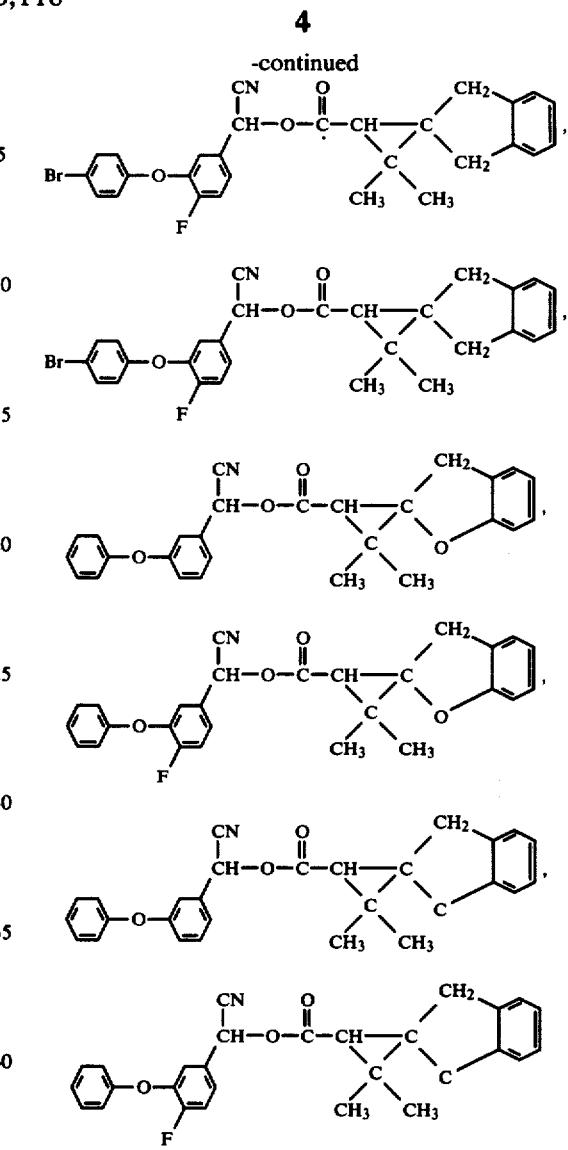

Based on this finding, the present invention has been accomplished.

Although, in connection with the present compounds, the related compounds have been exemplified in Japanese Patent Application "Kokai" (Laid-open) No. 105,045/76, yet all of the compounds of this invention are far superior in insecticidal and/or acaricidal activity to said related compounds.

The present carboxylate esters represented by the general formula (I) are novel compounds first synthesized by the present inventors. The methods of synthesizing these compounds are outlined below.

The present carboxylic ester is obtained (a) by the reaction of a carboxylic acid represented by the general formula (XI),

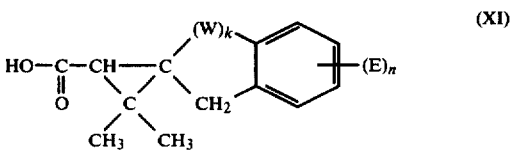

(XI)

wherein E, W, k and n are as defined above, or a reactive derivative thereof with an alcohol represented by the general formula (XII),

 (XII)

wherein X is as defined above and $R_{17}$ represents hydroxyl group, a halogen atom or toxyloxy group, or a reactive derivative thereof, if necessary, in the presence of a suitable solvent, reaction aid, or catalyst. The reactive derivatives of the carboxylic acids of the general formula (XI) include acyl halides and lower alkyl esters. When $R_2$ in the formulas (II) and (VIII) represents cyano group, the present carboxylic ester is obtained also (b) by the reaction of an aldehyde represented by the general formula (XIII) or (XIV),

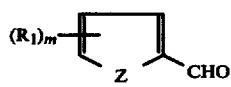 (XIII)

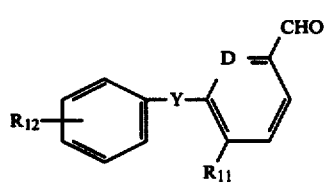 (XIV)

wherein $R_1$, $R_{11}$, $R_{12}$, D, Y, Z and m are as defined above, with an acyl halide represented by the general formula (XV),

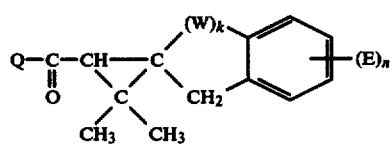 (XV)

wherein Q represents a halogen atom and E, W, k and n are as defined above, and an alkali metal cyanide.

Further, the carboxylic acids represented by the general formula (XI) are novel compounds which can be synthesized by the following synthetic routes:

Synthetic route (1)

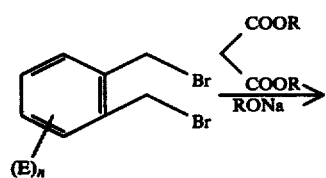

1

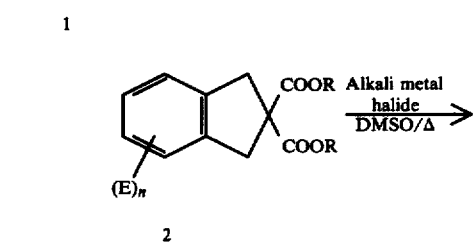

2

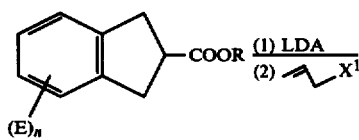

3

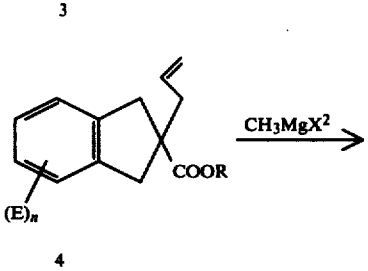

4

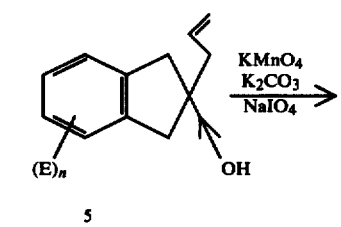

5

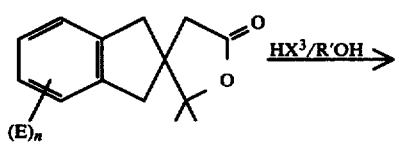

6

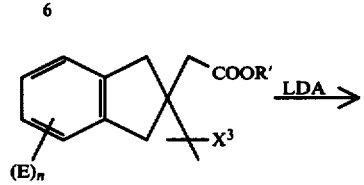

7

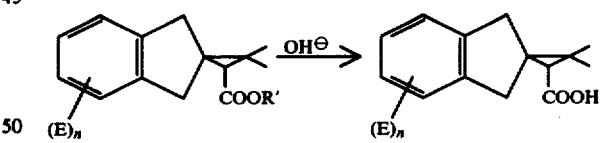

8    9

(wherein R and R' are $C_{1-3}$ alkyl group, $X^1$ is chlorine or bromine atom, $X^2$ is chlorine, bromine or iodine atom, $X^3$ is chlorine or bromine atom, and LDA means lithium diisopropyl amide.)

α-α'-Dibromoxylene (1) is reacted with a malonic ester in the presence of sodium alkoxide to obtain a diester (2) which is subsequently converted into a monoester (3) by heating in DMSO solution in the presence of an alkali metal halide. The monoester (3) is converted into an α-allyl monoester (4) by alkylation at the α-position with allyl halide which is subsequently subjected to a Grignard's reaction by methyl magnesium iodide to obtain a tertiary alcohol (5). The tertiary alcohol (5) is oxidized by the method of Periodate-permanganate oxidation (Lemieux oxidation) to form a lactone (6) which is subjected successively to ring opening with a hydrogen halide and an alcohol, ring closure with a strong base such as LDA, and hydrolysis to obtain a carboxylic acid (9).

Synthetic route (2)

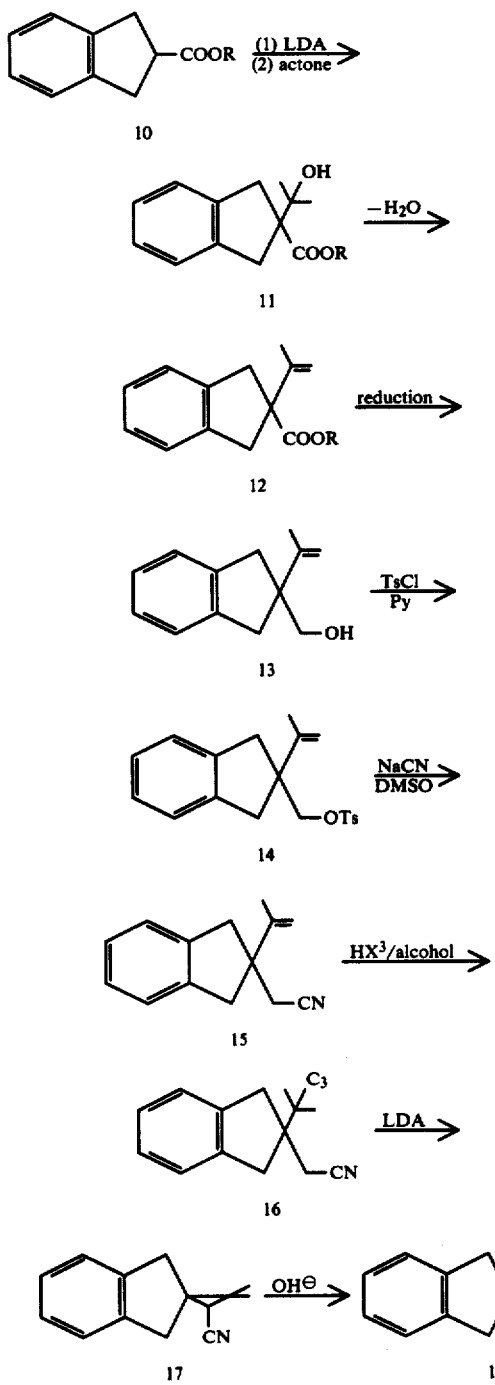

(wherein TsCl means tosylchloride and Py means pyridine.)

Acetone is added to the α-position of an indane-2-carboxylic ester (10) to form a tertiary alcohol (11) which is subsequently subjected to dehydration to obtain an α-isopropenyl monoester (12). And then the ester portion of an α-isopropenyl monoester (12) is reduced to an alcohol (13) which is then converted into a tosylate (14) and reacted with sodium cyanide to form a nitrile (15). After addition of a hydrogen halide to form a halogenated nitrile (16), the halogenated nitrile (16) is subjected successively to ring closure with a strong base such as LDA to form a cyclopropyl nitrile (17) and hydrolysis to obtain a carboxylic acid (18).

Synthetic route (3)

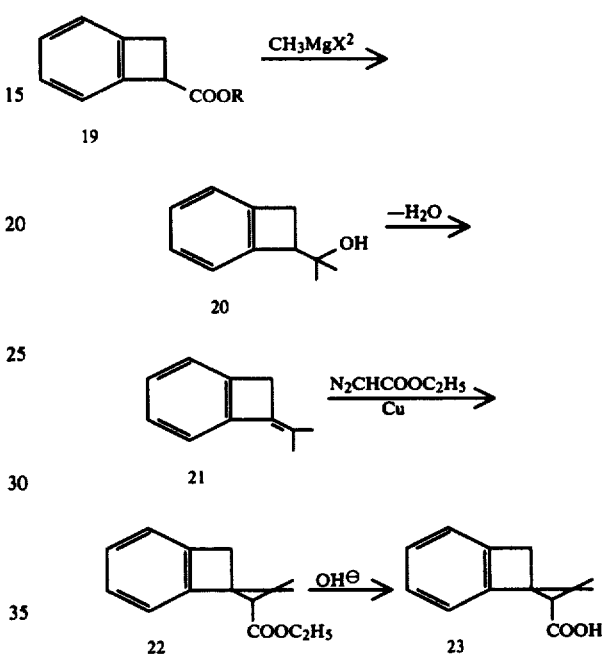

A benzocyclobutenecarboxylic ester (19) is converted into a tertiary alcohol (20) by the Grignard's reaction. The tertiary alcohol (20) is subjected to dehydration to form an olefin (21), and then the resulting olefin is reacted with a diazoacetic acid ester to obtain an ester (22) which is subsequently hydrolyzed to obtain a carboxylic acid (23).

Synthetic route (4)

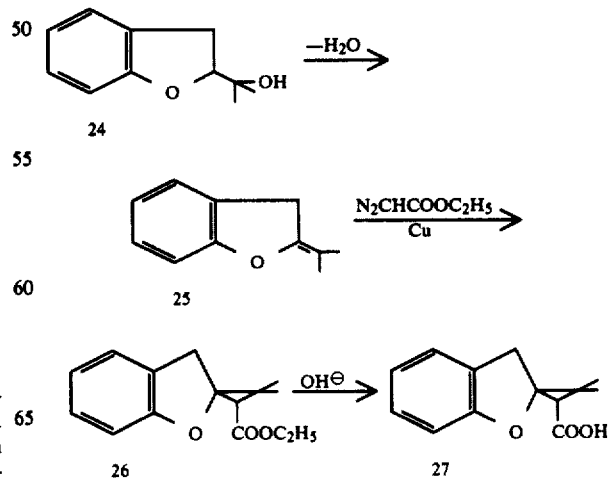

A carboxylic acid (27) is obtained from a tertiary alcohol (24) in a manner similar to that of synthetic route (3).

Synthetic route (5)

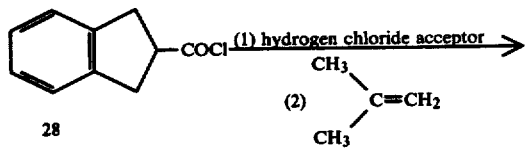

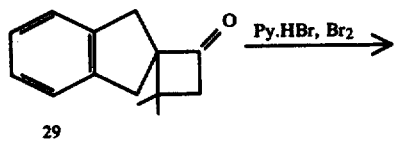

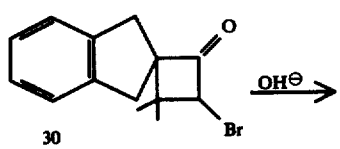

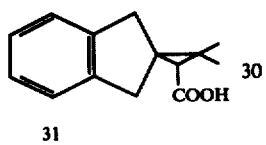

Inadane-2-carboxylic acid chloride (28) is reacted with an hydrogen chloride acceptor such as triethylamine or pyridine, and isobutene to obtain a four-membered ring compound (29) which is brominated to form a brominated compound (30). And then the brominated compound (30) is treated with a base to obtain a carboxylic acid (31).

From the carboxylic acid, it is possible to synthesize an acyl chloride, acyl bromide, and a lower ($C_{1-2}$) alkyl ester of carboxylic acid in the usual manner.

Examples of acid moieties or reactive derivatives thereof of the carboxylic acid ester (I) according to this invention are as shown below.

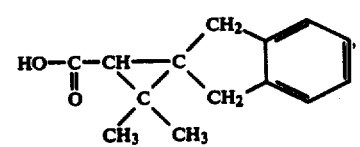

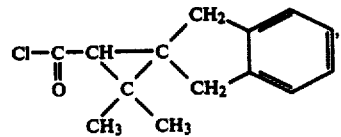

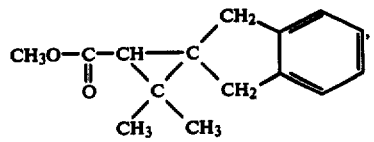

—continued

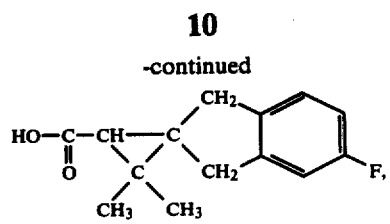

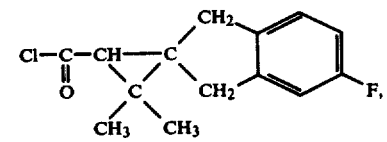

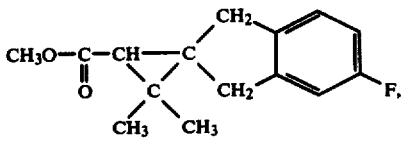

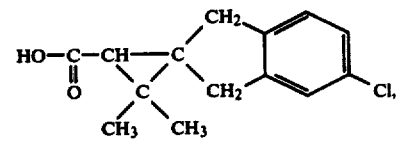

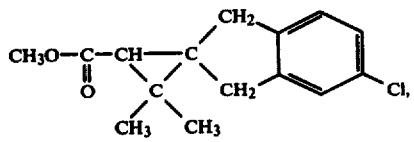

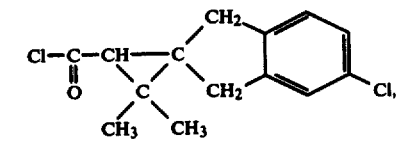

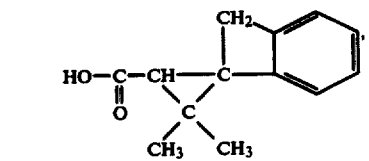

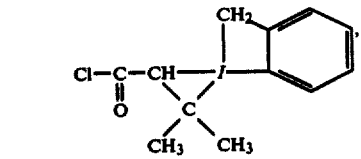

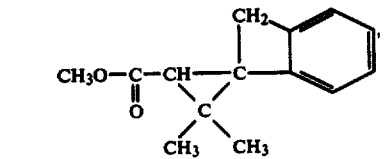

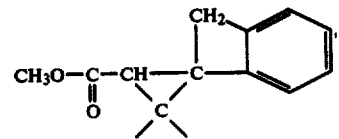

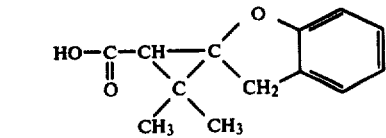

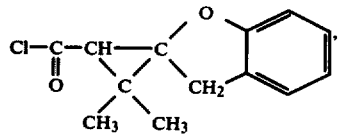
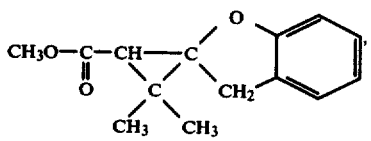
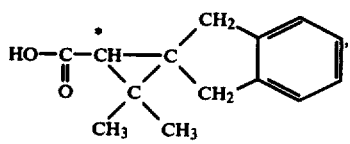
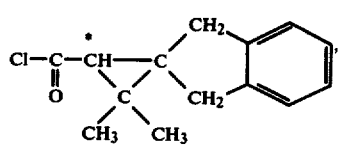
Examples of alcohol moieties of the carboxylic acid ester (I) according to this invention are as shown below.
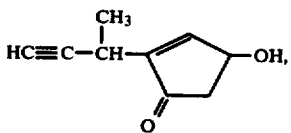
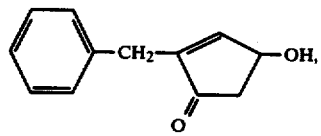
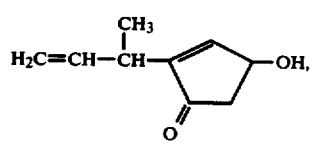
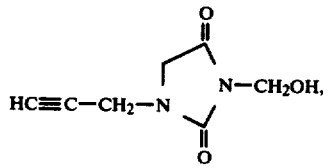
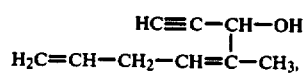
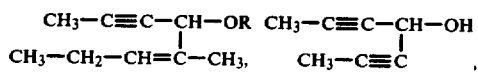
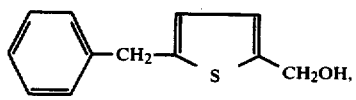
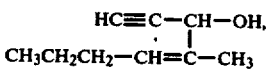
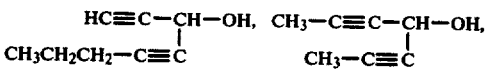
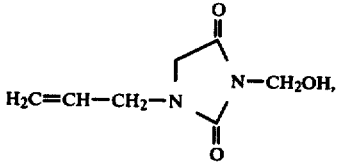
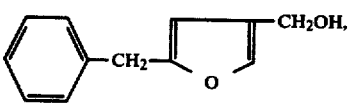
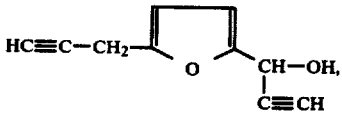
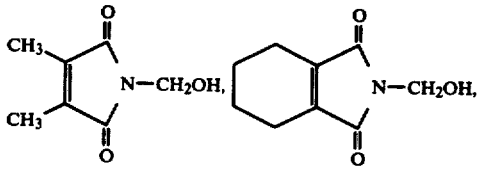
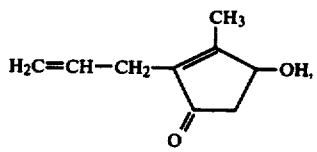
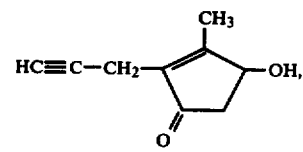
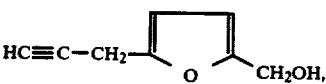
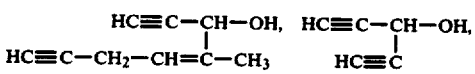
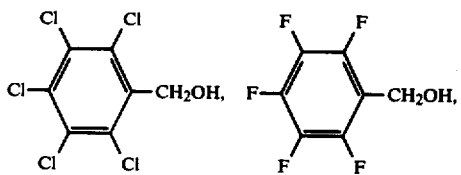
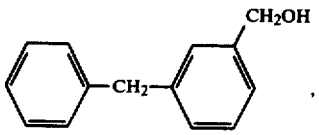

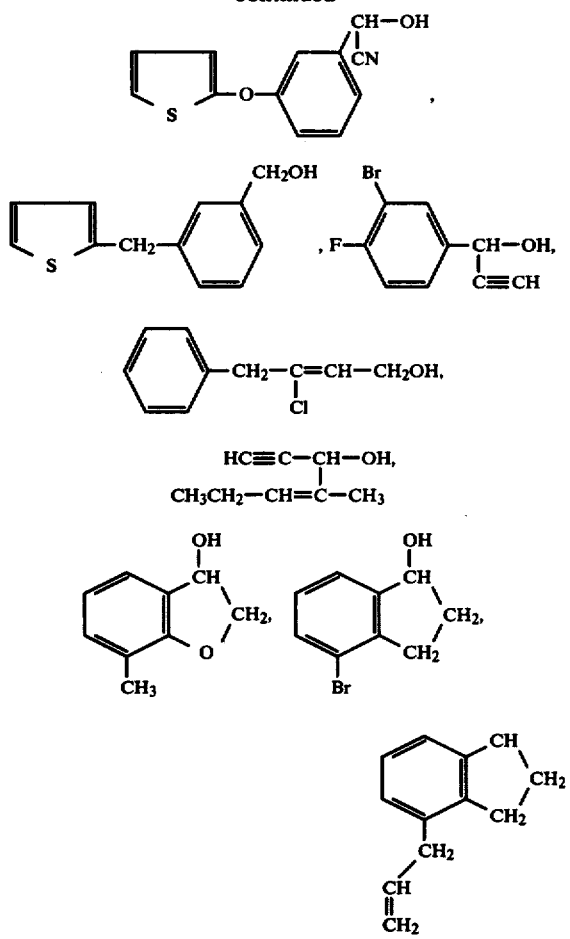

and alcohols represented by the general formula;

| Alcohol No. | R$_2$ | R$_{11}$ | R$_{12}$ | D | Y |
|---|---|---|---|---|---|
| 1 | —CN | H | H | —CH— | O |
| 2 | —CN | H | H | N | O |
| 3 | —CN | H | 4-Br | —CH— | O |
| 4 | —CN | H | 4-Cl | —CH— | O |
| 5 | —CN | H | 4-F | —CH— | O |
| 6 | —CN | H | 4-F | N | O |
| 7 | —CN | F | H | —CH— | O |
| 8 | —CN | F | 4-Cl | —CH— | O |
| 9 | —CN | F | 4-F | —CH— | O |
| 10 | —CN | F | 4-Br | —CH— | O |
| 11 | —CN | F | H | N | O |
| 12 | H | H | H | —CH— | O |
| 13 | H | F | H | —CH— | O |
| 14 | H | H | H | N | O |
| 15 | H | F | H | N | O |
| 16 | H | F | 4-Br | —CH— | O |
| 17 | H | F | 4-F | —CH— | O |
| 18 | H | F | 4-Cl | —CH— | O |
| 19 | —C≡CH | H | H | —CH— | O |
| 20 | —C≡CH | F | H | —CH— | O |
| 21 | —C≡CH | H | H | N | O |
| 22 | —C≡CH | F | H | N | O |
| 23 | —C≡CH | F | 4-Br | —CH— | O |
| 24 | —C≡CH | F | 4-Cl | —CH— | O |
| 25 | —C≡CH | H | 4-Br | —CH— | O |
| 26 | —C≡CH | H | 4-Br | N | O |
| 27 | —C≡C—CH$_3$ | H | H | —CH— | O |
| 28 | —C≡C—CH$_3$ | F | H | —CH— | O |
| 29 | —C≡C—CH$_3$ | H | H | N | O |
| 30 | —C≡C—CH$_3$ | F | 4-Br | —CH— | O |
| 31 | —C≡C—CH$_3$ | F | 4-F | —CH— | O |
| 32 | —CN | H | H | —CH— | —CH$_2$— |
| 33 | —CN | F | H | —CH— | —CH$_2$— |
| 34 | —CN | H | H | N | —CH$_2$— |
| 35 | —CN | H | H | —CH— | S |
| 36 | —CN | F | H | —CH— | S |
| 37 | —CN | H | H | —CH— | —NH— |
| 38 | —CN | F | H | —CH— | —NH— |
| 39 | —C≡CH | F | H | —CH— | —NH— |
| 40 | —C≡C—CH$_3$ | F | H | —CH— | —NH— |

*Explanation of symbols, R$_2$, R$_{11}$, R$_{12}$, D and Y, in the structure represented by the above formula.

Further, examples of compounds of this invention are as shown below, but the compounds of this invention are not limited to these examples.

| Compound No. | Chemical structural formula | Refractive index or melting point |
|---|---|---|
| 1 | (structure shown) | $n_D^{22.0}$ 1.5547 |
| 2 | (structure shown) | $n_D^{19.0}$ 1.5845 |

-continued

| Compound No. | Chemical structural formula | Refractive index or melting point |
|---|---|---|
| 3 | ![structure] 3-phenoxy-α-cyanobenzyl ester of 1-(2-(4-chlorobenzyl))-2,2-dimethylcyclopropanecarboxylic acid | $n_D^{21.5}$ 1.5884 |
| 4 | 3-phenoxy-α-cyanobenzyl ester with 4-F benzyl | $n_D^{28.0}$ 1.5748 |
| 5 | 3-phenoxy-α-cyanobenzyl ester with 4-Br benzyl | $n_D^{18.5}$ 1.5958 |
| 6 | 3-phenoxy-α-cyanobenzyl ester with 3-F benzyl | $n_D^{20.5}$ 1.5790 |
| 7 | 4-fluoro-3-phenoxy-α-cyanobenzyl ester with benzyl | $n_D^{22.0}$ 1.5748 |
| 8 | (S)-3-phenoxy-α-cyanobenzyl ester with benzyl | $n_D^{21.5}$ 1.5759 |
| 9 | (S)-3-phenoxy-α-cyanobenzyl ester with benzyl (acid moiety is optically active.) | $n_D^{20.0}$ 1.5821 |
| 10 | allethrolone ester (HC≡C—CH$_2$ cyclopentenone) with dibenzyl dimethylcyclopropane | $n_D^{21.5}$ 1.5552 |
| 11 | 5-benzyl-3-furylmethyl ester with dibenzyl dimethylcyclopropane | $n_D^{21.5}$ 1.5699 |

-continued

| Compound No. | Chemical structural formula | Refractive index or melting point |
|---|---|---|
| 12 | (phthalimide-N-CH₂-O-C(=O)-CH-C(CH₃)(CH₃)-[spiro-indane cyclopropane]) | m.p. 169–170° C. |
| 13 | (3-benzylbenzyl ester of spiro cyclopropane acid with CH₃, CH₃) | $n_D^{20.5}$ 1.5864 |
| 14 | (CH₃CH₂-CH=C(CH₃)-CH(C≡CH)-O-C(=O)-... CH₃ CH₃) | $n_D^{20.5}$ 1.5328 |
| 15 | (allethrolone ester ... CH₃ CH₃) | $n_D^{20.5}$ 1.5461 |
| 16 | (4-Br-phenoxy-α-cyano-3-phenoxybenzyl ester ... CH₃ CH₃) | $n_D^{18.0}$ 1.5963 |
| 17 | (α-cyano-3-phenoxybenzyl ester, oxaspiro, CH₃ CH₃) (cis) | $n_D^{30.0}$ 1.5840 |
| 18 | (α-cyano-3-phenoxybenzyl ester, oxaspiro, CH₃ CH₃) (trans) | $n_D^{29.0}$ 1.5805 |
| 19 | (α-cyano-3-phenoxybenzyl ester, spiro cyclobutane, CH₃ CH₃) | $n_D^{26.0}$ 1.5872 |
| 20 | (α-cyano-4-fluoro-3-phenoxybenzyl ester, spiro, CH₃ CH₃) | $n_D^{22.5}$ 1.5811 |

-continued

| Compound No. | Chemical structural formula | Refractive index or melting point |
|---|---|---|
| 21 | | $n_D^{20.5}$ 1.5864 |
| 22 | | $n_D^{21.5}$ 1.5630 |
| 23 | | $n_D^{22.0}$ 1.5475 |
| 24 | | $n_D^{23.0}$ 1.5352 |
| 25 | | $n_D^{23.0}$ 1.5513 |
| 26 | | $n_D^{22.0}$ 1.5804 |
| 27 | | $n_D^{21.0}$ 1.5284 |
| 28 | | $n_D^{30.0}$ 1.6102 |

| Compound No. | Chemical structural formula | Refractive index or melting point |
|---|---|---|
| 29 | (structure: benzyl-substituted cyclohexenone ester with 2,2-dimethyl-spiro[2,4]hept system bearing two CH₂-phenyl groups) | $n_D^{20.5}$ 1.5833 |

The methods of preparation of the present ester and the carboxylic acid moiety thereof are further illustrated below in detail with reference to Synthesis Examples and Reference Examples.

SYNTHESIS EXAMPLE 1

Synthesis of compound No. 2

Into 50 ml of dried toluene, were dissolved 2.25 g (0.01 mole) of α-cyano-3-phenoxybenzyl alcohol and 2.35 g (0.01 mole) of 2,2-dimethyl-5,6-benzospiro[2,4-]hept-5-ene-1-carbonyl chloride. To the resulting solution, with ice-cooling, was added dropwise 1.58 g (0.02 mole) of pyridine. After the addition was finished, the resulting mixture was stirred at room temperature for 5 hours to complete the reaction. The reaction mixture was poured into 50 ml of ice water. The toluene layer was separated and washed successively with 5% aqueous hydrochloric acid solution, saturated aqueous sodium hydrogencarbonate solution, and saturated aqueous sodium chloride solution, and then dried over anhydrous sodium sulfate and concentrated in vacuo. The residue obtained was purified by column chromatography on 80 g of silica gel (eluent: ethyl acetate-n-hexane (1:20) mixture) to give 3.55 g (84.0% in theoretical yield based on the carboxylic acid chloride used as starting material) of the intended ester in the form of colorless oil.

$n_D^{19.0}$ 1.5845.

NMR data (TMS, CDCl₃): δ: 1.48 (s, 1H); 2.60–3.62 (m, 4H), 6.25, 6.29 (1H, s); 6.83–7.50 (13H, m).

SYNTHESIS EXAMPLE 2

Synthesis of compound No. 4

Into 30 ml of dried acetone, were dissolved 0.82 g (2.84 mmoles) of α-cyano-3-phenoxybenzyl bromide and 0.36 g (3.59 mmoles) of dried triethylamine. To the resulting solution, was added dropwise over a period of 5 minutes at room temperature a solution of 0.70 g (2.99 mmoles) of 2,2-dimethyl-5,6-(m-fluorobenzo)spiro[2,4-]hept-5-ene-1-carboxylic acid in 20 ml of dried acetone. The resulting mixture was stirred for further 24 hours at room temperature to complete the reaction. The reaction mixture was poured into ice water and then extracted with ethyl acetate. The extract was washed successively with 3% aqueous hydrochloric acid solution, saturated aqueous sodium hydrogencarbonate solution, and saturated aqueous sodium chloride solution, then dried over anhydrous magnesium sulfate, and concentrated in vacuo to obtain an oily substance as the residue. This crude ester was purified by column chromatography on 40 g of silica gel (eluent: ethyl acetate-n-hexane (1:15) mixture) to give 0.77 g (61.5% in the theoretical yield based on the benzyl bromide used as starting material) of the intended carboxylic acid ester as a pale yellow oily substance.

$n_D^{28.0}$ 1.5748

NMR data (TMS, CDCl₃): δ: 1.50 (1H, s); 2.30–3.70 (4H, m); 6.28, 6.30 (1H, s); 6.6–7.6 (12H, m)

SYNTHESIS EXAMPLE 3

Synthesis of compound No. 4

Into 5 ml of water, were dissolved 0.49 g (10 mmoles) of sodium cyanide and 0.06 g (0.25 mmole) of benzyltriethylammonium chloride. To the resulting solution, was added dropwise with stirring at room temperature a mixture of 0.99 g (5 mmoles) of 3-phenoxybenzaldehyde, 1.23 g (5.25 mmoles) of 2,2-dimethyl-5,6-(m-fluorobenzo)spiro[2,4]hept-5-ene-1-carbonyl chloride, 10 ml of toluene, and 5 ml of n-heptane. After the addition was finished, the resulting mixture was stirred at the same temperature for 24 hours to complete the reaction. The reaction mixture was washed with saturated aqueous sodium chloride solution, dried over anhydrous sodium sulfate, and concentrated in vacuo. The resulting crude ester was purified by column chromatography on 50 g of silica gel (eluent: ethyl acetate-n-hexane (1:20) mixture) to obtain 1.78 g (80.7% in the theoretical yield based on the aldehyde used as starting material).

$n_D^{28.0}$ 1.5748

NMR data (TMS, CDCl₃) δ: 2.30–3.70 (4H, m); 6.28, 6.30 (1H, s); 6.6–7.6 (12H, m)

SYNTHESIS EXAMPLE 4

Synthesis of compounds No. 8 and No. 9

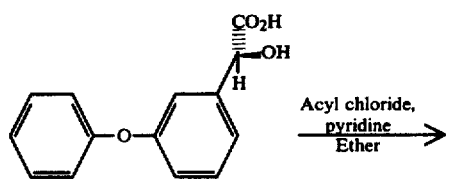

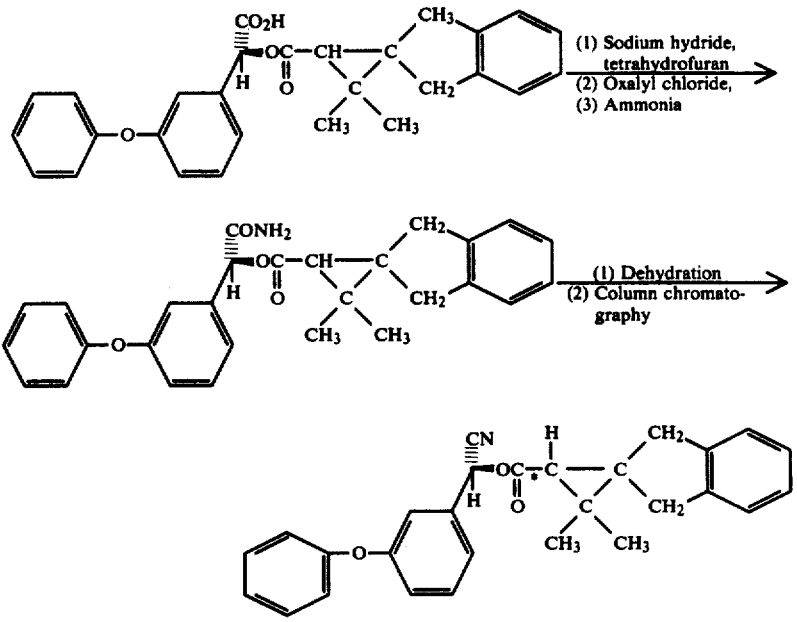

To a solution of 0.98 g of (S)-(+)-phenoxymandelic acid and 0.59 g of pyridine in 20 ml of ether, was added dropwise 1.03 g of 2,2-dimethyl-5,6-benzospiro[2,4]heptene-1-carbonyl chloride. After having been stirred for 12 hours, the reaction mixture was poured into 5% aqueous hydrochloric acid solution and extracted twice with ethyl acetate. The extract was washed with an aqueous sodium chloride solution, dried over magnesium sulfate, and evaporated in vacuo to obtain 1.94 g of a viscous oil. The oil was added portionwise to a solution of 0.190 g (62.4%) of sodium hydride in 20 ml of toluene. To the resulting mixture, with ice-cooling, was added 0.73 g of oxalyl chloride. After 3 hours of stirring, the reaction mixture was added to 30 ml of toluene saturated with ammonia, with ice-cooling, to yield an amide. The reaction mixture was added to 100 ml of cold 10% aqueous hydrochloric acid solution. And then toluene layer was separated. The toluene layer was washed with an aqueous sodium chloride solution, dried over magnesium sulfate, and concentrated in vacuo to obtain 2.05 g of a crude amide. Without having been purified, the crude amide was added to a solution of 0.93 g of pyridine in 40 ml of dioxane. To the resulting mixture, with ice-cooling, was added with stirring 2.5 g of trifluoroacetic anhydride. After having been stirred for 4 hours at 20° C., the mixture was poured into ice water and extracted with ethyl acetate. The ethyl acetate layer was washed with an aqueous sodium chloride solution, dried over magnesium sulfate and concentrated in vacuo to yield 1.85 g of an oil. The oil was subjected to column chromatography using 40 g of silica gel with a n-hexane-ethyl acetate (20:1) mixture as an eluent to obtain 0.78 g of a diastereomeric mixture, the acid portion of which being mixture of R- and S-configuration and the alcohol portion S-configuration.

$n_D^{21.5}$ 1.5759

NMR data (TMS, CDCl$_3$): δ: 1.12–1.55 (m, 7H); 2.9–3.65 (m, 4H); 6.28 (s), 6.32 (s) (1H in total, the methyne proton which bears the nitrile group); 6.9–7.5 (m, 13H)

Optical rotation: $[\alpha]_D^{23}$ +8.9° (c=0.56; diethyl ether)

The above diastereomeric mixture (0.70 g) was subjected to column chromatography with 40 g of silica gel (hexane-ethyl acetate (20:1) mixture as an eluent).

In NMR spectrum, the firstly eluted ester exhibited a singlet signal at δ6.28 due to the methyne proton which bears the nitrile group.

Eighty mg of secondarily eluted ester was obtained. It showed two sharp singlet peaks in NMR spectrum at δ6.28 and δ6.32 in a peak area of 15% and 85% respectively. Accordingly, its enantio excess on the acidic site was determined to be 70%. $n_D^{20.0}$ 1.5821

Optical rotation: $[\alpha]_D^{23}$ −4.3° (c=0.23, diethyl ether)

REFERENCE EXAMPLE 1

Synthesis of α,α'-dibromo-4-chloro-o-xylene

Into 300 ml of carbon tetrachloride, were added successively 50.0 g of 4-chloro-o-xylene, 133.02 g of N-bromosuccinimide (NBS), and 1.0 g of benzoyl peroxide. The mixture was heated under reflux with stirring for 4 hours. After completion of the reaction, the reaction mixture was cooled to room temperature and filtered. The filtrate was concentrated in vacuo to obtain 104.7 g of the intended product.

NMR data (TMS, CDCl$_3$): δ: 4.52 (2H, s); 4.54 (2H, s); 7.03–7.35 (3H, m)

Synthesis of 2,2-dimethoxycarbonyl-5-chloroindane

To a methanol solution of sodium methylate prepared from 16.04 g of sodium metal and 250 ml of methanol, with ice-cooling, was added a solution of 110.6 g of α,α'-dibromo-4-chloro-o-xylene in 100 ml of anhydrous ether. To the mixture, was added slowly a solution of 46.02 g of dimethyl malonate in 50 ml of anhydrous ether. The mixture was stirred for 48 hours at room temperature to complete the reaction. The reaction mixture was poured into a mixture of 100 ml of 1% aqueous hydrochloric acid solution and ice, and extracted with ether. The aqueous layer was extracted twice with ether. The ether layers were combined, washed with saturated aqueous sodium hydrogencarbonate solution, then with saturated aqueous sodium chloride solution, dried over anhydrous magnesium sulfate, and concentrated in vacuo to obtain 89.4 g of the intended product.

NMR data (TMS, CDCl₃): δ: 3.55 (4H, s); 3.73 (6H, s); 7.10 (3H, m)

Synthesis of methyl 5-chloroindane-2-carboxylate

To 300 ml of dimethyl sulfoxide, were added successively 64.0 g of 2,2-dimethoxycarbonyl-5-chloroindane, 5 ml of water and 10 g of lithium chloride. The mixture was heated with stirring for 3 hours at 120° to 130° C. The reaction mixture was cooled to room temperature poured into 500 ml of ice water, and mixed with ether. After the ether layer was separated, the aqueous layer was extracted twice with ether. The ether layers were combined, washed with saturated sodium chloride solution, dried over anhydrous magnesium sulfate, and concentrated in vacuo to obtain a crude product. The crude product was distilled in vacuo to obtain 15.97 g of the purified intended product. Boiling point, 113°–131° C./0.3 mmHg.

NMR data (TMS, CDCl₃): δ: 3.1–3.18 (5H, m); 3.65 (3H, s); 7.0–7.15 (3H, m)

Synthesis of methyl 2-allyl-5-chloroindane-2-carboxylate

To 50 ml of anhydrous tetrahydrofuran (THF), was added 4.37 g of diisopropylamine. To the mixture was added 29 ml of a hexane solution of n-butyllithium at −60° to −50° C. under a nitrogen stream. To the resulting solution, was added a solution of 7.0 g of methyl 5-chloroindane-2-carboxylate in 10 ml of anhydrous THF at −70° to −60° C. over a period of 10 minutes. After stirring for 30 minutes at the same temperature, a solution of 5.23 g of allyl bromide in 10 ml of anhydrous THF was added dropwise at −70° to −50° C. over a period of 10 minutes. The mixture was further stirred for 24 hours at room temperature to complete the reaction. The reaction mixture was poured into a mixture of 5% aqueous hydrochloric acid solution and ice, and mixed with ether. After the ether layer was separated, the aqueous layer was extracted twice with ether. The ether layers were combined, washed with saturated aqueous sodium hydrogencarbonate solution, then with saturated sodium chloride solution, dried over anhydrous magnesium sulfate, and concentrated in vacuo to obtain 8.32 g of the intended product.

NMR data (TMS, CDCl₃): δ: 2.40 (2H, d); 3.06 (4H, q); 3.61 (3H, s); 4.7–6.0 (3H, m); 6.95–7.05 (3H, m)

Synthesis of 2-allyl-5-chloro-2-(1-hydroxy-1-methylethyl)indane

To 150 ml of an anhydrous ether solution of methyl magnesium iodide prepared from 3.23 g of magnesium metal and 19.0 g of methyl iodide, with ice-cooling, was added dropwise a solution of 8.32 g of methyl 2-allyl-5-chloroindane-2-carboxylate in 10 ml of anhydrous ether. The mixture was stirred for 24 hours at room temperature to complete the reaction. The reaction mixture was poured into a mixture of saturated aqueous ammonium chloride solution and ice. After the ether layer was separated, the aqueous layer was extracted twice with ether. The ether layers were combined, washed with saturated sodium chloride solution, dried over anhydrous sodium sulfate, and concentrated in vacuo to obtain 7.56 g of the intended product.

NMR data (TMS, CDCl₃): δ: 1.12 (6H, s); 2.40 (2H, d); 4.7–5.9 (3H, m); 6.95–7.10 (3H, m)

Synthesis of 3,3-dimethyl-6,7-(m-chlorobenzo)-2-oxaspiro[4,4]non-6-en-1-one

Into 100 ml of methylene chloride, was dissolved 7.56 g of 2-allyl-2-(1-hydroxy-1-methylethyl)-5-chloroindane. Ozone generated from an ozonizer was introduced into the solution continuously at −40° C. for 5 hours to form an ozonide. To the resulting solution, with ice-cooling, was added 300 ml of a Jones reagent. The mixture was stirred for 24 hours at room temperature. And then the methylene chloride layer was separated and the aqueous layer was extracted twice with methylene chloride. The methylene chloride layers were combined, washed twice with saturated aqueous sodium chloride solution, dried over anhydrous magnesium sulfate, and concentrated in vacuo. The crude product obtained as the residue was purified by column chromatography on 250 g of silica gel (eluent:ethyl acetate-n-hexane (1:3)) to obtain 2.72 g of the purified intended product.

NMR data (TMS, CDCl₃): δ: 1.43 (6H, s); 2.50 (2H, s); 7.0–7.2 (3H, m)

Synthesis of methyl 2-(1-chloro-1-methylethyl)-5-chloroindane-2-acetate

Gaseous hydrogen chloride was introduced into 100 ml of anhydrous methanol cooled at −40° C. to obtain a methanol solution saturated with hydrogen chloride. To the resulting solution, was added 2.7 g of 3,3-dimethyl-6,7-(m-chlorobenzo)-2-oxaspiro[4,4]non-6-en-1-one followed by 6 ml of thionyl chloride. The mixture was left standing at −40° C. to room temperature for 24 hours and the reaction mixture was concentrated in vacuo. The residue was admixed with 100 ml of ether, washed twice with saturated aqueous sodium chloride solution, dried over anhydrous magnesium sulfate, and concentrated in vacuo to obtain 2.6 g of the intended product.

NMR data (TMS, CDCl₃): δ: 1.60 (6H, s); 2.59 (2H, s); 3.23 (3H, s)

Synthesis of methyl 2,2-dimethyl-5,6-(m-chlorobenzo)spiro[2,4]hept-5-ene-1-carboxylate Into 30 ml of anhydrous THF, was dissolved 1.22 g of dried diisopropylamine. To the solution, was added 7.5 ml of a hexane solution of butyllithium at −60° C. under a nitrogen stream. After stirring for 5 minutes at the same temperature, to the solution was added dropwise at −60° C. over a period of 10 minutes a solution of 2.6 g of methyl 2-(1-chloro-1-methylethyl)-5-chloroindane-2-acetate in 5 ml of anhydrous THF. After having been stirred for one hour, the reaction mixture was poured into 1% aqueous hydrochloric acid solution and admixed with ether. After the ether layer was separated, the aqueous layer was extracted twice with ether. The ether layers were combined, washed twice with saturated aqueous sodium chloride solution, dried over anhydrous magnesium sulfate, and concentrated in vacuo. The residue was purified by column chromatography on 20 g of silica gel (eluent:n-hexane-ethylacetate (10:1)) to obtain 1.0 g of the intended product.

NMR data (TMS, CDCl₃): δ: 1.28 (6H, s); 1.40 (1H, s); 3.58 (3H, s); 7.0–7.2 (3H, m)

Synthesis of 2,2-dimethyl-5,6-(m-chlorobenzo)-spiro[2,4]hept-5-ene-1-carboxylic acid To a solution comprising 1.5 g of potassium hydroxide, 15 ml of methanol and 1 ml of water, was added 0.9 g of methyl 2,2-dimethyl-5,6-(m-chlorobenzo)-spiro[2,4]hept-5-ene-1-carboxylate. The mixture was heated under reflux with stirring for 6 hours. After completion of the reaction, the reaction mixture was cooled to room temperature and concentrated in vacuo. After the residue was mixed with water and ether, the ether layer was discarded. Concentrated hydrochloric acid was added to the aqueous layer to adjust it to pH 1 and the mixture was extracted three times with ethyl acetate. The organic layers were combined, washed three times with saturated aqueous sodium chloride solution, dried over anhydrous magnesium sulfate, and concentrated in vacuo to obtain 0.7 g of the intended product as white crystals.

NMR data (TMS, deuteroacetone): δ: 1.39 (6H, s); 1.45 (1H, s); 2.6–3.6 (4H, m); 7.1–7.15 (3H, m)

REFERENCE EXAMPLE 2

Synthesis of 2-(1-hydroxy-1-methylethyl)-2-methoxycarbonylindane

To a dried THF solution of lithiumdiisopropylamide prepared from 107.3 ml (0.149 mole) of n-butyllithium and 15.81 g (0.156 mole) of diisopropylamine, was added dropwise at −50° C. a solution of 25.0 g (0.142 mole) of methyl indane-2-carboxylate in 50 ml of dried THF over a period of 10 minutes. To the resulting mixture, which had been stirred for 30 minutes at −50° C., was added dropwise over a period of 10 minutes a solution of 9.88 g (0.17 mole) of dried acetone in 10 ml of dried THF. After the addition, stirring was continued for further 10 minutes. The reaction mixture was poured into ice water and extracted with ether. The aqueous layer was extracted twice with ether. The ether layers were combined, washed successively with 3% aqueous hydrochloric acid solution, saturated aqueous hydrogen-carbonate solution, and saturated aqueous sodium chloride solution, then dried over anhydrous magnesium sulfate, and concentrated in vacuo to obtain the intended product as a oily substance.

NMR data (TMS, CDCl₃): δ: 1.12 (6H, s); 3.20 (2H, d); 3.51 (2H, d); 3.66 (3H, s); 7.10 (4H, s)

Synthesis of 2-isopropenyl-2-methoxycarbonylindane

Into 100 ml of dried pyridine, was dissolved 30.0 g (0.128 mole) of 2-(1-hydroxy-1-methylethyl)-2-methoxycarbonylindane. To the solution, was added dropwise 39.4 g (0.256 mole) of phosphorus oxychloride over a period of 30 minutes at room temperature. The mixture was heated at 100° C. to continue the reaction for further 4 hours. The reaction mixture was cooled to room temperature, poured into a mixture of 10% aqueous hydrochloric acid solution and ice, and extracted with ether. The aqueous layer was extracted twice with ether. The ether layers were combined, washed successively with water, saturated aqueous sodium hydrogencarbonate solution, and saturated aqueous sodium chloride solution, dried over anhydrous magnesium sulfate, and concentrated in vacuo to obtain the intended product as a oily substance.

NMR data (TMS, CDCl₃): δ: 1.78 (3H, m); 3.04 (2H, d); 3.57 (2H, d); 3.58 (3H, s); 4.84 (2H, m); 7.05 (4H, s).

Synthesis of 2-isopropenyl-2-indanemethanol

To 50 ml of dried ether containing 0.86 g (0.018 mole) of lithium aluminum hydride, with ice-cooling, was added dropwise over a period of 10 minutes a solution of 4.15 g (0.018 mole) of 2-methoxycarbonyl-2-isopropenylindane in 10 ml of dried ether. The mixture was then stirred at room temperature for 2 hours to continue the reaction. The reaction mixture was poured into a mixture of 5% aqueous hydrochloric acid solution and ice. And then the ether layer was separated and the aqueous layer was extracted twice with 25 ml of ether. The ether layers were combined, washed with saturated aqueous sodium hydrogencarbonate solution, then with saturated aqueous sodium chloride solution, dried over anhydrous sodium sulfate, and concentrated in vacuo to obtain 3.23 g of 2-isopropenyl-2-indanemethanol.

NMR data (TMS, CDCl₃): δ: 7.05 (4H, s); 4.90 (2H, m); 3.40 (2H); 1.80 (3H, s).

Synthesis of 2-isopropenyl-2-indanylmethyl tosylate

To a mixture of 3.20 g (0.017 mole) of 2-isopropenyl-2-indanemethanol and 3.16 g (0.04 mole) of pyridine, with ice-cooling, was added 3.90 g (0.02 mole) of tosylchloride. The mixture was stirred for 24 hours, with ice-cooling, to complete the reaction. The reaction mixture was poured into ice water, mixed with 50 ml of ether. And then the ether layer was separated, the aqueous layer was extracted twice with 25 ml of ether. The ether layers were combined, washed with 2% aqueous hydrochloric acid solution, then with saturated aqueous sodium chloride solution, dried over anhydrous sodium sulfate, and concentrated in vacuo to obtain 5.80 g of 2-iso-propenyl-2-indanylmethyl tosylate.

NMR data (TMS, CDCl₃): δ: 7.70 (2H, d); 7.25 (2H, d); 7.02 (4H, s); 4.82 (2H, m); 3.90 (2H, s); 2.40 (3H, s); 1.70 (3H, s)

Synthesis of 2-isopropenyl-2-indanylacetonitrile

To a solution of 6.20 g (0.018 mole) of 2-isopropenyl-2-indanylmethyl tosylate in 50 ml of dried dimethyl sulfoxide, was added 1.80 g (0.036 mole) of finely ground sodium cyanide. The mixture was then stirred at 100° C. for 8 hours to complete the reaction. After cooling, the reaction mixture was poured into ice water, and mixed with 50 ml of ether. And then the ether layer was separated, and the aqueous layer was extracted twice with 25 ml of ether. The ether layers were combined, washed with 5% aqueous hydrochloric acid solution, then with saturated aqueous sodium chloride solution, dried over anhydrous magnesium sulfate, and concentrated in vacuo. The residue was purified by column chromatography on 50 g of silica gel (eluent-:acetate-n-hexane (1:5)) to obtain 1.80 g of the purified intended product.

NMR data (TMS, CDCl₃): δ: 7.11 (4H, s); 5.00 (2H, m); 3.20 (2H, d); 2.78 (2H, d); 2.50 (2H, s); 1.90 (3H, s)

Synthesis of 2-(1-chloro-1-methylethyl)-2-indanylacetonitrile

Dried hydrogen chloride gas was introduced into 20 ml of dried methanol, with ice-cooling, to obtain a methanol solution saturated with hydrogen chloride. To the resulting methanol solution, was added 0.50 g (0.00254 mole) of 2-isopropenyl-2-indanylacetonitrile. The mixture was stirred for 24 hours at room temperature and the reaction mixture was concentrated in vacuo to obtain 0.60 g of the intended product.

NMR data (TMS, CDCl$_3$): δ: 7.10 (4H, s); 2.7-3.5 (4H, m); 1.70 (2H, s); 1.62 (6H, s)

Synthesis of 1-cyano-2,2-dimethyl-5,6-benzospiro[2,4]hept-5-ene

To a solution of 0.40 g (0.00386 mole) of diisopropylamine in 20 ml of dried THF, was added at −60° C. 2.6 ml (0.00386 mole) of a n-hexane solution of n-butyllithium under a nitrogen stream. To the resulting solution, was added at −60° C. dropwise over a period of 5 minutes a solution of 0.60 g (0.00257 mole) of 2-(1-chloro-1-methylethyl)-2-indanylacetonitrile in 5 ml of dried THF. The mixture was gradually brought to room temperature and stirred at room temperature for 24 hours. The reaction mixture was poured into a mixture of 5% aqueous hydrochloric acid solution and ice, and admixed with ether. And then the ether layer was separated, the aqueous layer was extracted twice with 30 ml of ether. The ether layers were combined, washed with saturated aqueous sodium hydrogen-carbonate solution, then with saturated aqueous sodium chloride solution, dried over anhydrous sodium sulfate, and concentrated in vacuo to obtain 0.47 g of the intended product.

NMR data (TMS, CDCl$_3$): δ: 7.15 (4H, s); 2.6-3.5 (4H, m); 1.28 (3H, s); 1.30 (3H, s)

Synthesis of 2,2-dimethyl-5,6-benzospiro[2,4]hept-5-ene-1-carboxylic acid

Into a mixture of 10 ml of ethylene glycol and 2 ml of water, was dissolved 1.0 g (0.0179 mole) of potassium hydroxide. To the solution, was added 0.7 g (0.00355 mole) of 1-cyano-2,2-dimethyl-5,6-benzospiro[2,4]hept-5-ene. The mixture was heated under reflux at 120° to 130° C. for 10 hours. After cooling, 60 ml of water and 20 ml of ether were added to the reaction mixture. And then the aqueous layer was separated, and admixed with concentrated hydrochloric acid to adjust the pH to 1-2. The aqueous layer was extracted twice with 30 ml of toluene. The toluene layers were combined, washed with saturated aqueous sodium chloride solution, dried over anhydrous magnesium sulfate, and concentrated in vacuo to obtain 0.4 g of the intended product.

NMR data (TMS, CDCl$_3$): δ: 7.10 (4H, s); 2.6-3.6 (4H, m); 1.42 (1H, s); 1.30 (6H, s)

Melting point: 212.8° C.

REFERENCE EXAMPLE 3

Synthesis of 1-(1-hydroxy-1-methylethyl)-benzocyclobutene

To an ether solution of methylmagnesium iodide prepared from 1.2 g of magnesium and 7.01 g of methyl iodide, was added dropwise a solution of 2.0 g of methyl benzocyclobutenecarboxylate in 10 ml of dried ether over a period of 10 minutes at room temperature under a nitrogen atmosphere. After stirring for 24 hours at room temperature, the reaction mixture was poured into a cold aqueous ammonium chloride solution. And then the ether layer was separated, and the aqueous layer was extracted twice with ether. The ether layers were combined, washed twice with saturated aqueous sodium chloride solution, dried over anhydrous magneisum sulfate, and concentrated in vacuo to obtain 1.89 g of the intended product as the residue.

NMR data (TMS, CDCl$_3$): δ: 1.29 (3H, s); 1.37 (3H, s); 3.08 (2H, d); 3.55 (1H, dd); 6.98-7.35 (4H, m)

Synthesis of 1-isopropylidenebenzocyclobutene

Into 30 ml of dried pyridine, was dissolved 1.78 g of 1-(1-hydroxy-1-methylethyl)benzocyclobutene. To the solution, was added dropwise 3.37 g of phosphorus oxychloride over a period of 5 minutes at room temperature. The mixture was stirred for 24 hours at room temperature, then poured into 3% aqueous cold hydrochloric acid solution and admixed with ether. After the ether layer was separated, the aqueous layer was extracted twice with ether. The ether layers were combined, washed with saturated aqueous sodium hydrogencarbonate solution, then with saturated aqueous sodium chloride solution, dried over anhydrous magnesium sulfate, and concentrated in vacuo to obtain as the residue 1.5 g of a mixture of the intended product and 1-isopropenylbenzocyclobutene. This mixture was used without further purification as the starting material in the next step of preparation.

Synthesis of methyl 2,2-dimethyl-4,5-benzospiro[2,3]hept-4-enecarboxylate

A mixture of 1.5 g of crude 1-isopropylidenebenzocyclobutene obtained as above and 0.1 g of copper powder was heated at 100° C. To the mixture, was added dropwise 2.4 g of ethyl diazoacetate over a period of 5 minutes. The mixture was kept at the same temperature for 10 minutes to continue the reaction. The reaction mixture was cooled to room temperature, removed of the copper powder by filtration, then passed downward through a column packed with 80 g of silica gel (eluent:n-hexane-ethyl acetate (20:1)) to obtain about 1 g of an oily product. The oily product was hydrolyzed with 10 ml of 10% methanol solution of potassium hydroxide.

The resulting solution was mixed with water and ether. And then the ether layer was discarded, and the aqueous layer was acidified with aqueous hydrochloric acid solution and extracted with ethyl acetate. The ethyl acetate layer was washed with saturated sodium chloride solution, dried over anhydrous magnesium sulfate, and concentrated in vacuo to obtain 0.6 g of an oily substance. The oily substance was converted into methyl ester with diazomethane and purified by column chlomatography on Lobar ® column (size B, eluent:n-hexane-ethyl acetate (100:1)) to obtain 0.25 g of the intended methyl ester (a mixture of cis and trans isomers).

NMR data (TMS; CDCl$_3$): δ: 1.30-1.41 (6H, m); 1.95, 1.98 (1H, s); 3.63, 3.65 (3H, s); 7.00-7.40 (4H, m).

Synthesis of 2,2-dimethyl-4,5-benzospiro[2,3]hept-4-enecarboxylic acid

Into 10 ml of a 10% methanol solution of potassium hydroxide, was dissolved 0.2 g of methyl 2,2-dimethyl-4,5-benzospiro[2,3]hept-4-ene-carboxylate. The mixture was stirred at 60° C. for 6 hours, and then at room temperature for 24 hours. The reaction mixture was mixed with 70 ml of water and 50 ml of ether. The ether layer was discarded and the aqueous layer was acidified with 10% aqueous hydrochloric acid solution and extracted with ethyl acetate. The ethyl acetate layer was washed three times with saturated sodium chloride solution, dried over anhydrous magnesium sulfate, and concentrated in vacuo to obtain 0.13 g of the intended carboxylic acid.

NMR data (TMS; CDCl$_3$): δ: 1.28–1.40 (6H, m); 1.91, 1.95 (1H, s); 3.00–3.60 (2H, m); 7.00–7.35 (4H, m)

REFERENCE EXAMPLE 4

Synthesis of 2-(1-methyl-1-hydroxyethyl)-2,3-dihydrobenzofuran

Into 200 ml of ethanol, was dissolved 10.3 g of 2-(1-methyl-1-hydroxyethyl)benzofuran. To the solution, was added 1.1 g of 10% palladium carbon. Hydrogen was introduced into the mixture with shaking at atmospheric pressure and at room temperature until no more hydrogen had been absorbed (it took 6 hours). The reaction mixture was filtered and the filtrate was concentrated in vacuo. The residue was distilled under reduced pressure to obtain 6.86 g of the intended product boiling at 78°–95° C./0.4 mmHg.

NMR data (TMS, CDCl$_3$): δ: 1.2 (3H, s); 1.4 (3H, s); 3.11 (2H, d); 4.55 (1H, dd)

Synthesis of 2-isopropylidene-2,3-dihydrobenzofuran

Into 40 ml of dried pyridine, was dissolved 6.6 g of 2-(1-methyl-1-hydroxyethyl)-2,3-dihydrobenzofuran. To the solution, with ice-cooling, was added dropwise 11.38 g of phosphorus oxychloride over a period of 10 minutes. After the addition was finished, the mixture was stirred for 2 hours at room temperature and poured into ice water. After ether was added to the mixture, the ether layer was separated and the aqueous layer was extracted twice with 50 ml of ether. The ether layers were combined, washed successively with 5% aqueous hydrochloric acid solution, saturated aqueous sodium hydrogencarbonate solution and saturated aqueous sodium chloride solution, then dried over anhydrous magnesium sulfate, and concentrated in vacuo to obtain 5.7 g of the crude 2-isopropylidene-2,3-dihydrobenzofuran. This crude product contained 2-isopropylbenzofuran, 2-isopropenyl-2,3-dihydrobenzofuran and small amount of many other unidentifiable impurities, in addition to the intended product. However, because of labileness of the intended product, the crude product was used in the starting material without further purification in the next preparative step.

Synthesis of ethyl 2,2-dimethyl-4-oxa-5,6-benzospiro[2,4]hept-5-ene-1-carboxylate To a solution of 4.0 g of crude 2-isopropylidene-2,3-dihydrobenzofuran obtained as above in 10 ml of xylene, was added 1 g of copper powder. To the mixture, while being kept at 120° C., was added dropwise 8 g of ethyl diazoacetate over a period of 10 minutes. The mixture was stirred for further 10 minutes at the same temperature, then cooled, removed of the copper powder by filtration, and concentrated in vacuo. The residue was passed downward through a column packed with 200 g of silica gel (Art 7734 of Merck Co.; eluent:n-hexane-ethyl acetate (10:1) mixture) and the fractions showing Rf of 0.5–0.9 on TLC (n-hexane-ethyl acetate (3:1)) were collected. The collected fractions were concentrated and added to a mixture of 60 ml of methanol, 2 ml of water and 10.2 g of potassium hydroxide. The resulting mixture was stirred for 24 hours at room temperature to complete hydrolysis. The reaction mixture was concentrated in vacuo. The residue was mixed with water and ether and the ether layer was discarded. The aqueous layer was acidified with 10% aqueous hydrochloric acid solution and extracted with ethyl acetate. The ethyl acetate layer was washed twice with water, dried over anhydrous magnesium sulfate, and concentrated in vacuo to obtain 1.3 g of the crude carboxylic acid. It was esterified with 10 ml of DMF, 3 g of triethylamine and 6 g of ethyl bromide to obtain 1.4 g of crude ethyl ester. The crude ester was purified by column chromatography on Lober ® column (size B; eluent:n-hexane-ethyl acetate (100:1)) to obtain 0.3 g of the intended ethyl ester.

The carboxylic ester obtained as described above was a cis-isomer. A trans-isomer was obtained by carrying out the diazotization in n-hexane with an organic copper complex*) as catalyst, and purifying as described above.

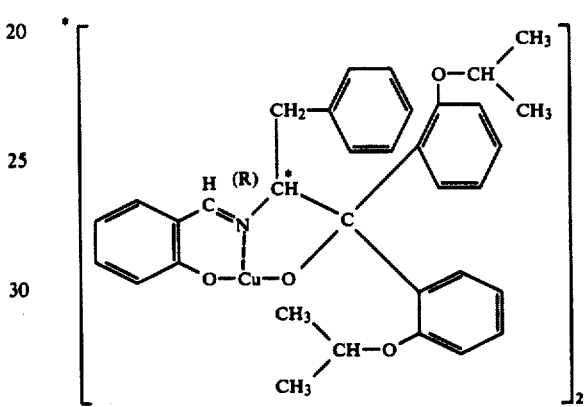

| NMR data (TMS, CDCl$_3$): | |
|---|---|
| δ, cis-isomer | δ, trans-isomer |
| 1.20 (3H, s) | 1.30 (3H, s) |
| 1.50 (3H, s) | 1.48 (3H, s) |
| 3.00 (1H, d) | 1.90 (1H, s) |
| 3.48 (1H, d) | 3.30 (1H, d) |
| 4.05 (2H, q) | 3.75 (1H, d) |
| 6.6–7.2 (4H, m) | 6.6–7.2 (4H, m) |

Synthesis of 2,2-dimethyl-5,6-benzo-4-oxaspiro[2,4]hept-5-ene-1-trans-carboxylic acid:

Into a 10% methanol solution of potassium hydroxide, was dissolved 870 mg of ethyl 5,6-benzo-2,2-dimethyl-4-oxaspiro[2,4]hept-5-ene-1-trans-carboxylate. The solution was stirred at room temperature for 24 hours, then concentrated in vacuo, and mixed with water and ether. The aqueous layer was separated, acidified with aqueous 10% hydrochloric acid solution and extracted with ethyl acetate. The ethyl acetate layer was washed twice with water, dried over anhydrous magnesium sulfate and concentrated in vacuo to obtain 680 mg of the crude carboxylic acid. Melting point, 144.6° C. (uncorr.) (impurities content, 20%)

NMR data (TMS, CDCl$_3$): δ: 1.41 (3H, s); 1.48 (3H, s); 1.81 (1H, s); 3.30 (1H, d); 3.76 (1H, d); 6.7–7.4 (4H, m)

REFERENCE EXAMPLE 5

Synthesis of 3,3-dimethyl-6,7-benzospiro[3,4]oct-6-en-1-one

Into an autoclave containing 70 ml of cyclohexane, were charged 10.0 g of indanyl-2-carbonyl chloride and 2 g of isobutene. To the mixture in the autoclave, was added dropwise 6.1 g of triethylamine over a period of 1.5 hours at 60° C., while continuously introducing isobutene. After 8 hours of reaction, the reaction mixture was poured into ice water and extracted twice with ethyl acetate. The ethyl acetate layers were combined, washed with an aqueous sodium chloride solution, dried over magnesium sulfate, and concentrated in vacuo. The residue was purified by column chromatography on silica gel to obtain 5.0 g (45% yield) of 3,3-dimethyl-6,7-benzospiro[3,4]oct-6-en-1-one.

NMR data (TMS, CDCl$_3$): δ: 1.27 (6H, s); 2.83 (2H, s); 3.06 (4H, s); 7.08 (4H, s)

Synthesis of 5,6-benzo-2,2-dimethyl-spiro[2,4]hept-5-one-1-carboxyliac acid:

To 20 ml of acetic acid, was added 2.0 g of 3,3-dimethyl-6,7-benzospiro[3,4]oct-6-en-1-one followed by 3.0 g of pyridinium bromide perbromide. The mixture was stirred for 2 hours at 50° C. The reaction mixture was poured into ice water, and extracted twice with ethyl acetate. The combined ethyl acetate layer was washed with water, dried over magnesium sulfate and concentrated in vacuo. The residual oil was added to a mixture of an aqueous sodium hydroxide solution (4.2 g of sodium hydroxide in 38 ml of water) and 20 ml of toluene. To the mixture, was added 30 ml of benzyltriethylammonium chloride. The resulting mixture was stirred for 12 hours at 20° C. The reaction mixture was poured into water and the toluene layer was removed. The aqueous layer was adjusted to pH 1 with aqueous 10% hydrochloric acid solution, and extracted twice with diethyl ether. The combined ether layer was washed with an aqueous sodium chloride solution, then dried over magnesium sulfate, and concentrated in vacuo. The residual oil was subjected to silica gel column chromatography (eluent: hexaneethyl acetate (5/1-1/1) to obtain 1.33 g (62% yield) of 5,6-benzo-2,2-dimethylspiro[2,4]hept-5-ene-1-carboxylic acid.

In formulating insecticidal or acaricidal compositions from the present compounds represented by the general formula (I), any of the preparations suitable for application may be prepared similarly to conventional pyrethroid insecticides in a manner well known to those skilled in the art by using the active components and those diluting agents which are generally used in conventional insecticidal composition. The forms of such preparations include emulsifiable concentrates, wettable powders, dusts, granules, oil sprays, aerosols, heating fumigants (e.g., mosquito coil, electrical mosquito killer, etc.), fogging preparations, non-heating fumigants, and poisonous baits. In the practical application, preparations containing 0.01 to 90% by weight of the active ingredient are generally used.

Further, the insecticidal activity of the present compound may be enhanced by using together with known synergists for pyrethroids such as α-[2-(2-butoxyethoxy)ethoxy]-4,5-methylenedioxy-2-propyltoluene ("piperonylbutoxide") and octachlorodipropyl ether ("S-421").

If necessary, compositions more stable in activity may be obtained by adding suitable amounts of stabilizers such as antioxidants or ultraviolet absorbers including, for example, phenol or bisphenol derivatives such as BHT and BHA; arylamines such as phenyl-α-naphthylamine, phenyl-β-naphthylamine, and phenetidine-acetone condensates; and benzophenone compounds.

Furthermore, multi-purpose compositions of excellent activities may be prepared by mixing with other biologically active substances such as, for example, allethrin, tetramethrin, phenothrin, d-trans- or di-cis,-trans-chrysanthemic acid esters thereof, pyrethrum extract, d-trans- or d-cis,trans-chrysanthemic acid ester of d-allethrolone, fenvalerate and other known pyrethroids; organophosphates insecticides such as fenitrothion, cyanophos and dichlovos; carbamates such as carbaryl and MPMC; other insecticides, fungicides, nematicides, acaricides, herbicides, plant growth regulators, fertilizers, microbial agrochemicals such as BT preparation and BM preparation, insect hormone preparations, and other agrochemicals. Even a synergistic effect might be expected from such joint use.

The preparation and activity of the insecticidal and/or acaricidal compositions of this invention are illustrated below with reference to Preparation Examples and Test Examples.

PREPARATION EXAMPLE 1

Oil spray 0.1 Part of each compound Nos. 10, 12, 15, 17, 18, 19, 22, 23 and 29 of this invention is dissolved in deodorized kerosene and made up to 100 parts with kerosene to obtain an oil spray.

PREPARATION EXAMPLE 2

Emulsifiable concentrate

Each 20 parts of the present compounds No. 1 to No. 29, 10 parts of an emulsifier (Sorpol 3005X; trademark for Toho Chemical Co.) and 70 parts of xylene are thoroughly mixed by stirring to obtain an emulsifiable concentrate of each compound.

PREPARATION EXAMPLE 3

Aerosol

Prescribed amounts of each active compound and tetramethrin or resmethrin, as shown in the following Table, are dissolved in a mixture of xylene and deodorized kerosene and filled in an aerosol container. After attaching the valve portion to the container, a propellant (LPG) is charged into the container through the valve under pressure to obtain an aerosol.

| Compound No. | Active compound | Tetramethrin | Resmethrin | Xylene | Deodorized kerosene | Propellant |
|---|---|---|---|---|---|---|
| 1 | 0.05 | 0.2 | — | 2.5 | 57.25 | 40 |
| 3 | 0.05 | 0.2 | — | 2.5 | 57.25 | 40 |
| 5 | 0.05 | 0.2 | — | 2.5 | 57.25 | 40 |
| 10 | 0.45 | — | 0.05 | 5 | 44.5 | 50 |
| 11 | 0.2 | 0.3 | — | 5 | 44.5 | 50 |
| 12 | 0.45 | — | 0.05 | 5 | 44.5 | 50 |
| 22 | 0.45 | — | 0.05 | 5 | 44.5 | 50 |
| 23 | 0.45 | — | 0.05 | 5 | 44.5 | 50 |
| 23 | 0.2 | 0.3 | — | 5 | 44.5 | 50 |

PREPARATION EXAMPLE 4

Wettable powder

Each 10 parts of the present compounds Nos. 10 to 15, 17 to 20, 22 and 23, 5 parts of an emulsifier (Sorpol 5029-0; trademark for Toho Chemical Co.) and 85 parts of 300-mesh diatomaceous earth are thoroughly mixed in a mortar to obtain a wettable powder.

PREPARATION EXAMPLE 5

Dust

Each 0.5 part of the present compounds Nos. 1, 3 to 6, 10 to 16, 19, 22, 23, and 27 to 29 is dissolved in an appropriate amount of acetone, then admixed with 99.5 parts of 300-mesh talc, thoroughly mixed, and freed from the acetone by evaporation to obtain a dust preparation.

PREPARATION EXAMPLE 6

Mosquito coil

Each 0.6 g of the present compounds Nos. 10, 16 and 27 is dissolved in 20 ml of methanol and uniformly mixed with 99.4 g of a carrier for mosquito coils (a mixture of Tabu powder, pyrethrum marc and wood powder in a proportion of 3:5:1) by thorough stirring. After evaporation of methanol and addition of 150 ml of water, the mixture is thoroughly kneaded, then molded, and dried to obtain a mosquito coil.

The compositions of this invention prepared as described above showed insecticidal and/or acaricidal activities as shown below.

TEST EXAMPLE 1

Insecticidal activity against housefly (Filter paper bait and contact method)

A piece of filter paper, 5.5 cm in diameter, was laid on the bottom of a polyethylene cup of the identical inner diameter. An emulsifiable concentrate prepared in the same manner as in Preparation Example 2 was diluted with water. To the filter paper, was added dropwise 0.7 ml of the diluted sample (500 ppm in concentration). Sucrose (30 mg) was placed on the filter paper to serve as bait. Ten adult female houseflies were released into the cup, closed with a cover, and observed for the number of dead and alive insects after 48 hours to calculate the mortality (2 replications).

| Compound No. | Mortality (%) |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 100 |
| 28 | 100 |
| 29 | 100 |
| Untreated | 0 |

TEST EXAMPLE 2

Insecticidal activity against housefly (Topical application method)

The present compounds and the reference compounds were diluted with acetone to prescribed concentrations. Each 0.5 μl of the diluted samples was applied topically with a microsyringe onto the dorsal thorax of an adult female housefly. The flies were fed and observed for the number of dead and alive insects after 24 hours. $LD_{50}$ (median lethal dose) was calculated from the mortalities at each dosage by probit method.

| Compound No. | $LD_{50}$ μg/female |
|---|---|
| 1 | 0.0052 |
| 2 | 0.0045 |
| 3 | 0.0076 |
| 4 | 0.0042 |
| 5 | 0.018 |
| 7 | 0.0044 |
| 8 | 0.0032 |
| 9 | 0.0013 |
| 11 | 0.023 |
| 17 | 0.064 |
| 18 | 0.0061 |
| 23 | 0.045 |
| (1) | 0.26 |
| (2) | 0.079 |
| (3) | 0.070 |
| (4) | 0.16 |

Note:
[1] Compound described in Japanese Patent Publication No. 21,473/'71.
[2] Compound described in U.S. Pat. No. 3,835,176.
[3] Compound described in Japanese Unexamined Patent Application "Kokai" (Laid-open) No. 112,881/'78.
[4] Compound described in Japanese Unexamined Patent Application "Kokai" (Laid-open) No. 105,040/'76.

TEST EXAMPLE 3

Insecticidal activity against green rice leafhopper

A 20% emulsifiable concentrate was prepared from the present composition prepared in Preparation Example 2 and the emulsifiable concentrate was diluted 4,000 fold with water. A rice plant grown in a 180-ml plastic cup for one month from the sowing was sprayed with the diluted emulsifiable concentrate (50 ppm in concentration) at a rate of 15 ml per 2 cups on a turntable. After air drying, the cups were covered with a wire-screen cage and about 15 carbamate and organophosphate-resistant adult green rice leafhoppers were released into the cage. After 24 hours, the number of dead and alive insects was observed. For the purpose of examining the residual activity, the insects were released likewise at 3 days and 7 days after the spraying and the number of dead and alive insects was observed after 24 hours. (2 replications)

| Compound No. | Percent mortality days after spraying | | |
|---|---|---|---|
| | 0 | 3 | 7 |
| 1 | 100 | 100 | 86 |
| 2 | 100 | 100 | 100 |
| 3 | 100 | 100 | 100 |
| 5 | 100 | 100 | 100 |
| 7 | 100 | 100 | 100 |
| 13 | 100 | 93 | 100 |
| 16 | 100 | 100 | 97 |
| 20 | 100 | 100 | 90 |
| NAC* | 50 | 10 | 0 |
| BPMC** | 13 | — | — |
| Untreated | 0 | 3 | 0 |

Note:
*Reference Example - A 2,000-fold dilution of 1-naphthyl N—methylcarbamate 50% wettable powder (equivalent to 250 ppm solution).
**Reference Example - A 1,000-fold dilution of 2-sec-butylphenyl N—methylcarbamate 25% emulsifiable concentrate (equivalent to 250 ppm solution).

TEST EXAMPLE 4

Insecticidal activity against tobacco cutworm

An artificial diet (15 g) for tobacco cutworm was wet with 2 ml of the prescribed aqueous dilution of an emulsifiable concentrate obtained in Preparation Example 2 or of that obtained from reference compounds. The diet thus treated was placed in a polyethylene cup of 11 cm in diameter. Ten third-instar larvae of tobacco cutworm were released into the cup and the number of dead and alive insects was observed after 24 hours to determine the median lethal concentration ($LC_{50}$) (4 replications).

| Compound No. | $LC_{50}$ (ppm) |
|---|---|
| 1 | 3.5 |
| 2 | 2.0 |
| 3 | 3.3 |
| 4 | 1.0 |
| 5 | 7.2 |
| 7 | 1.8 |
| 8 | 1.1 |
| 9 | 0.6 |
| 18 | 1.8 |
| 19 | 5.0 |
| 25 | 4.0 |
| 28 | 8.7 |

| Compound No. | $LC_{50}$ (ppm) |
|---|---|
| (structure with CH$_2$—O—C(=O)—CH—CH, cyclopropyl, CH=C(CH$_3$)$_2$)* | 24.0 |
| (structure with CH(CN)—O—C(=O)—CH—C, cyclopropyl, dihydroindene)** | 46.1 |

Note:
*Compound described in Japanese Unexamined Patent Publication No. 21,473/'71
**Compound (described in Japanese Patent Application "Kokai" (Laid-open) No. 105,040/76.

TEST EXAMPLE 5

Controlling effect on carmine mite

Adult female carmine mite was allowed to parasitize at a rate of 10 mites per leaf on a non-climbing kidney bean plant of primoridal leaf stage grown in a pot for 5 days after sowing. The plant was then kept in a constant temperature room at 27° C. After 6 days, an emulsion prepared by diluting an emulsifiable concentrate obtained as in Preparation Example 2 with water (500 ppm) was sprayed over the plant on a turntable at a rate of 10 ml per pot. After 10 days, the number of adult female mites on the plant was counted. The criterion was as follows:

| Criterion | Number of adult female mites per leaf |
|---|---|
| ++ | 0–9 |
| + | 10–30 |
| − | 31 or more |

The results obtained were as shown in the following Table.

| Compound No. | Efficacy |
|---|---|
| 1 | ++ |
| 2 | ++ |
| 3 | ++ |
| 4 | ++ |
| 7 | ++ |
| 8 | ++ |
| 9 | ++ |
| 11 | ++ |
| 18 | ++ |
| Chlorodimeform* | ++ |
| Untreated | − |

Note:
*A 1,000-fold dilution of a 50% emulsifiable concentrate of N'—(2-methyl-4-chlorophenyl)- N,N—dimethylformamidine was used.

TEST EXAMPLE 6

Activity against adult housefly and adult female northern house mosquito

Ten adult houseflies and ten adult female northern house mosquitos were released in a glass chamber, 70 × 70 × 70 cm in size. An oil spray preparation (0.5 ml) obtained in Preparation Example 1 was sprayed inside the chamber and the insects were exposed to the descending mist for 10 minutes, during which time the number of knocked-down insects was counted at predetermined time intervals to determine the 50% knockdown time ($KT_{50}$). On the following day, the dead and alive insects were observed.

| Compound No. | $KT_{50}$ (sec.) - mortality (%) | |
|---|---|---|
| | House fly | Northern house mosquito |
| 10 | 210–30 | 320–100 |
| 12 | 125–10 | 400–95 |
| 15 | 250–20 | 300–95 |
| 17 | 264–80 | 330–100 |
| 18 | 600–10 | 456–100 |
| 19 | 600–80 | 492–100 |
| 22 | 80–90 | 344–10 |
| 23 | 388–60 | 360–70 |
| 29 | 298–40 | 296–70 |
| (1) | >600– —(2) | 600–50 |

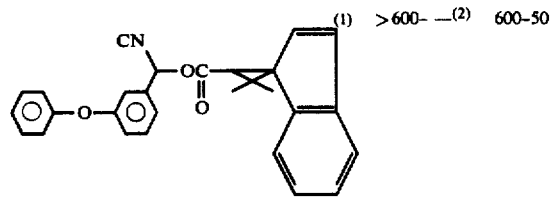

Note:
(1)Compound described in Japanese Unexamined Patent Application "Kokai" (Laid-open) No. 105,040/76.
(2)Since there were few knocked-down insects, the mortality could not be determined.

TEST EXAMPLE 7

About 50 adult female northern house mosquitos were released into a glass chamber, 70×70×70 cm, and a battery-operated small fan (diameter of rotation of the vane: 13 cm) disposed in the cabinet was operated. A mosquito coil obtained in Preparation Example 6 was ignited at both ends and placed at the center of bottom of the chamber. After 20 minutes, the number of knocked down insects was counted.

| Compound No. | Percent knocked down insects after 20 minutes (%) |
|---|---|
| 10 | 94 |
| 15 | 90 |
| 27 | 10 |

What is claimed is:
1. A carboxylic acid ester represented by the general formula,

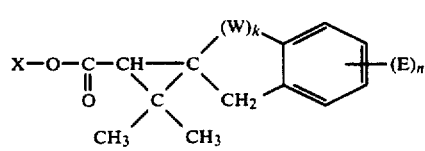

wherein X is represented by the formula,

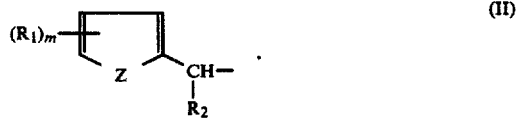

$R_1$ being hydrogen or halogen atom, or methyl, 2-propenyl, 2-propynyl, benzyl, 2-cyclopenten-1-yl, thienyloxy or thenyl group, $R_2$ being hydrogen atom, or ethynyl, cyano or 1-propynyl group, Z being oxygen or sulfur atom, or —CH═CH— group and m being an integer of 1 to 3 when Z is oxygen or sulfur atom and being an integer of 1 to 5 when Z is —CH═CH— group; provided that when $R_1$ is benzyl group, Z is oxygen or sulfur atom;

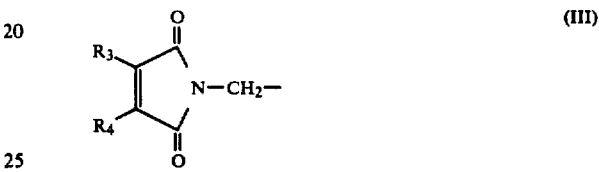

$R_3$ and $R_4$ being methyl group or bonded at the ends to form tetramethylene chain;

$R_5$ being hydrogen atom or methyl group and $R_6$ being benzyl, 1-buten-3-yl or 1-butyn-3-yl group when $R_5$ is hydrogen atom and $R_6$ being ethyl, 2-propenyl, 3-chloro-2-propenyl or 2-propynyl group when $R_5$ is methyl group;

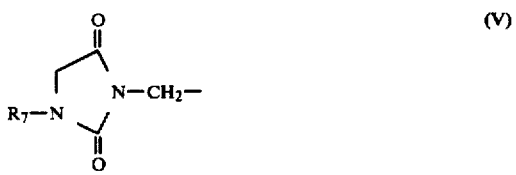

$R_7$ being 2-propenyl or 2-propynyl group;

$R_8$ being hydrogen atom or methyl group and $R_9$ being a group of the formula,

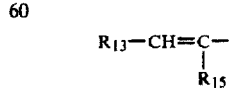

($R_{13}$ is $C_{1-3}$ alkyl, 2-propenyl, 2-propynyl or benzyl group and $R_{15}$ is hydrogen atom or methyl group) or $R_{14}$—C≡C— ($R_{14}$ is hydrogen atom or $C_{1-3}$ alkyl, 2-propenyl, 2-propynyl or benzyl group);

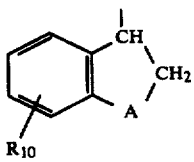

$R_{10}$ being hydrogen or halogen atom, or methyl or 2-propenyl group and A being oxygen atom or methylene group;

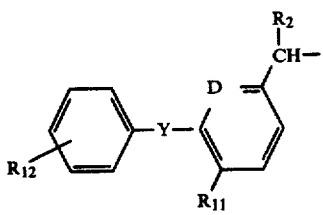
(VIII)

$R_{11}$ being hydrogen or fluorine atom, $R_{12}$ being hydrogen, chlorine, fluorine or bromine atom, D being CH group or nitrogen atom, and Y being oxygen or sulfur atom, or —$CH_2$— or —NH— group, and $R_2$ being as defined above; or

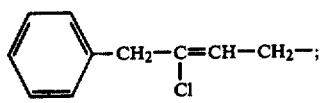
(IX)

W is oxygen atom or —$CH_2$— group; k is an integer of 0 or 1; E is hydrogen, chlorine, fluorine or bromine atom; and n is an integer of 1 to 4.

2. The carboxylic acid ester according to claim 1, wherein X is represented by the formula (VIII) wherein D is CH group, and Y is oxygen atom and $R_2$, $R_{11}$ and $R_{12}$ are as defined in claim 1; E is hydrogen, chlorine or fluorine atom.

3. The carboxylic acid ester according to claim 2 having the following formula,

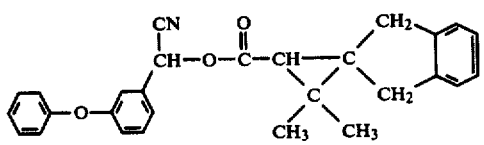

4. The carboxylic acid ester according to claim 2 having the following formula,

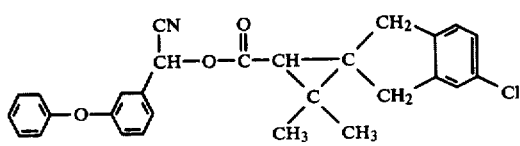

5. The carboxylic acid ester according to claim 2 having the following formula,

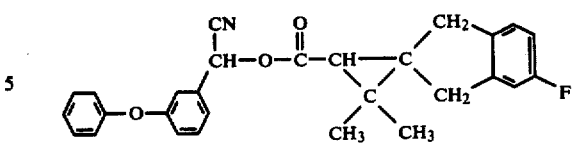

6. The carboxylic acid ester according to claim 2 having the following formula,

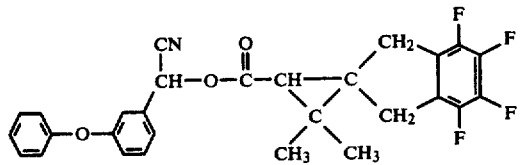

7. The carboxylic acid ester according to claim 2 having the following formula,

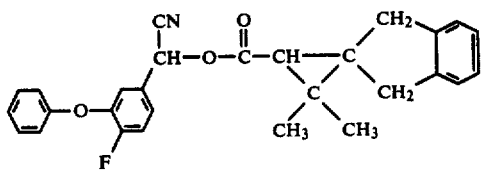

8. The carboxylic acid ester according to claim 2 having the following formula,

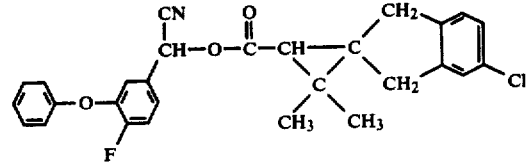

9. The carboxylic acid ester according to claim 2 having the following formula,

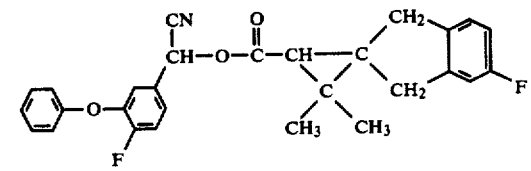

10. The carboxylic acid ester according to claim 2 having the following formula,

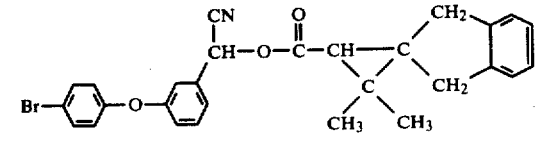

11. The carboxylic acid ester according to claim 2 having the following formula,

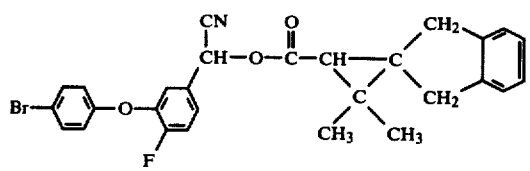

12. The carboxylic acid ester according to claim 2 having the following formula,

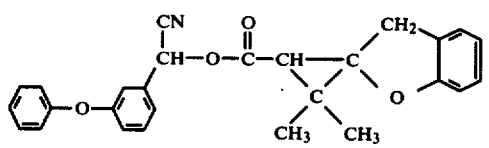

13. The carboxylic acid ester according to claim 2 having the following formula,

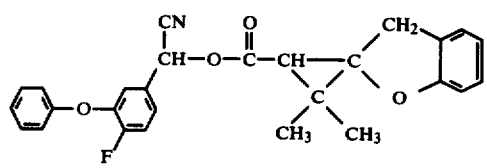

14. The carboxylic acid ester according to claim 2 having the following formula,

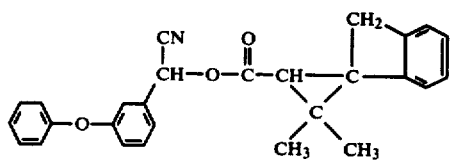

15. The carboxylic acid ester according to claim 2 having the following formula,

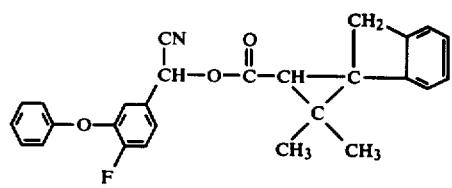

16. An insecticidal and/or acaridical composition comprising an inert carrier and, as an active ingredient an insecticidally and/or acaricidally effective amount of the carboxylic acid ester according to claim 1.

17. A carboxylic acid or a reactive derivative thereof represented by the general formula,

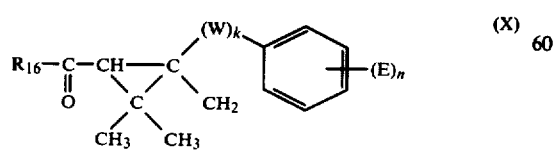

wherein $R_{16}$ is hydroxy group, chlorine or bromine atom, or a $C_{1-2}$ alkoxy group, W is oxygen atom or —$CH_2$— group, k is an integer of 0 or 1, E is hydrogen, chlorine, fluorine or bromine atom, and n is an integer of 1 to 4.

18. The carboxylic acid or the reactive derivative thereof according to claim 17, wherein $R_{16}$ is hydroxy group, chlorine atom or a $C_{1-2}$ alkoxy group, and E is hydrogen, chlorine or fluorine atom.

19. The carboxylic acid according to claim 18 having the following formula,

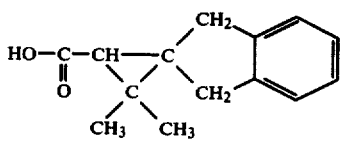

20. The reactive derivative of carboxylic acid according to claim 18 having the following formula,

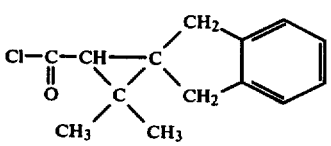

21. The reactive derivative of carboxylic acid according to claim 18 having the following formula,

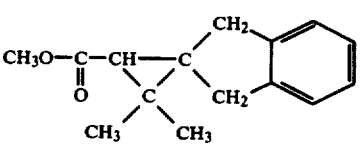

22. The carboxylic acid according to claim 18 having the following formula,

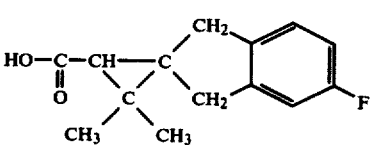

23. The reactive derivative of carboxylic acid according to claim 18 having the following formula,

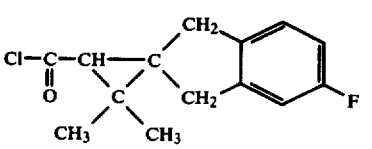

24. The reactive derivative of carboxylic acid according to claim 18 having the following formula,

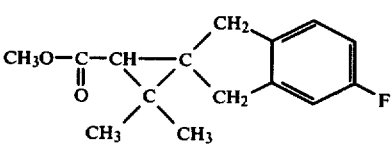

25. The carboxylic acid according to claim 18 having the following formula,

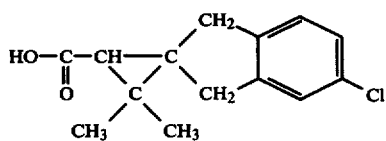

26. The reactive derivative of carboxylic acid according to claim 18 having the following formula,

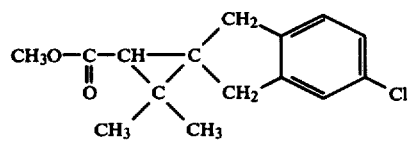

27. The reactive derivative of carboxylic acid according to claim 18 having the following formula,

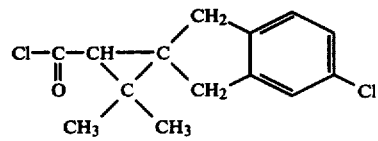

28. The carboxylic acid according to claim 18 having the following formula,

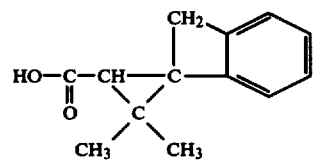

29. The reactive derivative of carboxylic acid according to claim 18 having the following formula,

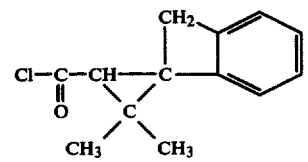

30. The reactive derivative of carboxylic acid according to claim 18 having the following formula,

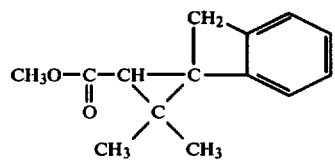

31. The carboxylic acid according to claim 18 having the following formula,

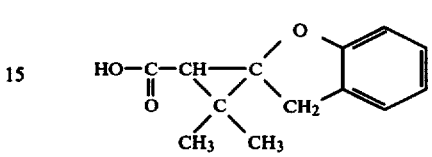

32. The reactive derivative of carboxylic acid according to claim 18 having the following formula,

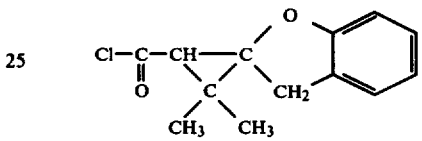

33. The reactive derivative of carboxylic acid according to claim 18 having the following formula,

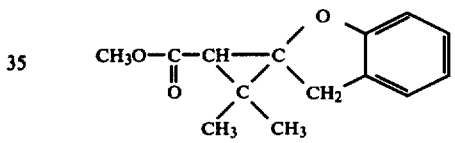

34. The optically active carboxylic acid according to claim 18 having the following formula,

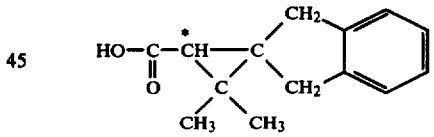

35. The reactive derivative of optically active carboxylic acid according to claim 18 having the following formula,

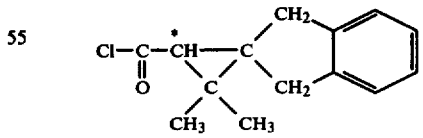

* * * * *